US006927030B2

(12) United States Patent
Huang et al.

(10) Patent No.: US 6,927,030 B2
(45) Date of Patent: Aug. 9, 2005

(54) METHODS OF DETECTING AND TREATING MICROSATELLITE-INSTABILITY POSITIVE TUMORS USING RIZ

(75) Inventors: Shi Huang, San Diego, CA (US); Robert B. Chadwick, Castro Valley, CA (US)

(73) Assignees: The Burnham Institute, La Jolla, CA (US); The Ohio State University, Columbus, OH (US)

( * ) Notice: Subject to any disclaimer, the term of this patent is extended or adjusted under 35 U.S.C. 154(b) by 36 days.

(21) Appl. No.: 10/024,450

(22) Filed: Dec. 17, 2001

(65) Prior Publication Data

US 2003/0032606 A1 Feb. 13, 2003

Related U.S. Application Data

(60) Provisional application No. 60/256,582, filed on Dec. 19, 2000.

(51) Int. Cl.[7] .......................... C07H 21/04; C12Q 1/68
(52) U.S. Cl. ........................ 435/6; 435/91.1; 435/91.2; 536/23.1; 536/24.3
(58) Field of Search .......................... 435/6, 91.1, 91.2; 536/23.1, 24.3

(56) References Cited

U.S. PATENT DOCUMENTS

| 5,811,304 A | 9/1998 | Huang | 435/325 |
| 5,831,008 A | 11/1998 | Huang | 530/350 |
| 6,069,231 A | 5/2000 | Huang | 530/327 |

OTHER PUBLICATIONS

Sasaki et al. (Blood, vol. 96, vol. 11, Part I, p. 704a, Nov. 2000).*
Aaltonen et al., "Incidence of hereditary nonpolyposis colorectal cancer and the feasibility of molecular screening for the disease," *New Eng. J. Med.* 338:1481–1487 (1998).
Abbondanza et al., "The retinoblastoma–interacting zinc–finger protein RIZ is a downstream effector of estrogen action," *Proc. Natl. Acad. Sci. USA* 97:3130–3135 (2000).
Boland et al., "A national cancer institute workshop on microsatellite instability for cancer detection and familial predesposition: Development of international criteria for the determination of microsatellite instablility in colorectal cancer," *Cancer Res.* 58:5248–5257 (1998).
Buyse et al., "The retinoblastoma protein binds to RIZ, a zinc–finger protein that shares an epitope with the adenovirus E1A protein," *Proc. Natl. Acad. Sci. USA* 92:4467–4471 (1995).
Canzian et al., "Semiautomated assessment of loss of heterozygosity and replication error in tumors," *Cancer Res.* 56:3331–3337 (1996).
Chadwick et al., "Candidate tumor suppressor RIZ is frequently involved in colorectal carcinogenesis," *Proc. Natl. Acad. Sci. USA* 97:2662–2667 (2000).

Claij et al., "Microsatellite instability in human cancer: a prognostic marker for chemotherapy?," *Exp. Cell Res.* 246:1–10 (1999).
Du et al., "Hypermethylation in human cancers of the RIZ1 tumor suppressor gene, a member of a histone/protein methyltransferase superfamily," *Cancer Res.* 61(22):8094–8099 (2001).
Fang et al., "Mapping of a minimal deleted region in human hepatocellular carcinoma to 1p36.13–p36.23 and mutational analysis of the RIZ (PRDM2) gene localized to the region," *Genes, Chromosomes & Cancer* 28(3):269–275 (2000).
Fang et al., "Preferential loss of a polymorphic RIZ allele in human hepatocellular carcinoma," *British J. Cancer* 84(6):743–747 (2001).
Garriga et al., "Migrations of the *Caenorhabditis elegans* HSNs are regulated by egl–43, a gene encoding two zinc finger protiens," *Genes Devel.* 7:2097–2109 (1993).
He et al., "RIZ1, but not the alternative RIZ2 product of the same gene, is underexpressed in breast cancer, and forced RIZ1 expression causes G2–M cell cycle arrest and/or apoptosis," *Cancer Res.* 58:4238–4244 (1998).
Huang, "The retinoblastoma protein–interacting zinc finger gene RIZ in 1p36–linked cancers," *Frontiers in Bioscience* 4: D528–532 (1999).
Huang et al., "The PR domain of the Rb–binding zinc finger protein RIZ1 is a protein binding interface and is related to the SET domain functioning in chromatin–mediated gene expression," *J. Biol. Chem.* 273:15933–15939 (1998).
Jiang et al., "The yin–yang of PR–domain family genes in tumorigenesis," *Histol. Histopathol.* 15:109–117 (2000).
Jiang and Huang, "Decreased RIZ1 expression but not RIZ2 in hepatoma and suppression of hepatoma tumorigenicity by RIZ1," *Intl. J. Cancer* 83:541–546 (1999).
Jiang and Huang, "Adenovirus expressing RIZ1 in tumor suppressor gene therapy of microsatellite–unstable colorectal cancer," *Cancer Res.* 61(5):1796–1798 (2001).
Kim et al., "Accumulated frameshift mutations at coding nucleotide repeats during the progression of gastric carcinoma with microsatellite instability," *Lab. Invest.* 79:1113–1120 (1999).

(Continued)

*Primary Examiner*—Jeanine A. Goldberg
(74) *Attorney, Agent, or Firm*—McDermott Will & Emery LLP

(57) ABSTRACT

The invention provides a method of inhibiting growth of a microsatellite instability (MSI)-positive tumor. The method is practiced by introducing into an MSI-positive tumor a nucleic acid molecule encoding a RIZ1 polypeptide and expressing the RIZ1 polypeptide in the tumor in an effective amount to inhibit growth of the tumor. Also provided is a method of determining the MSI status of a tumor. The method is practiced by determining in the tumor the number of adenosine (A) nucleotides in a poly(A) tract of a RIZ nucleic acid molecule in the tumor. An abnormal number of adenosine nucleotides in a RIZ poly(A) tract indicates that the tumor is MSI-positive.

7 Claims, 7 Drawing Sheets

OTHER PUBLICATIONS

Knudson, "Mutation and cancer: statistical study of retinoblastoma," *Proc. Natl. Acad. Sci. USA* 68:820–823 (1971).

Kong et al., "PTEN1 is frequently mutated in primary endometrial carcinomas," *Nat. Genet.* 17:143–144 (1997).

Leygue et al., "Expression of lumican in human breast carcinoma," *Cancer Res.* 58:1348–1352 (1998).

Liu et al., "The retinoblastoma interacting zinc finger gene RIZ produces a PR domain–lacking product through an internal promoter," *J. Biol. Chem.* 272:2984–2991 (1997).

Mao et al., "Microsatellite alterations as clonal markers for the detection of human cancer," *Proc. Natl. Acad. Sci. USA* 91:9871–9875 (1994).

Morishita et al., "Retroviral activation of a novel gene encoding a zinc finger protein in IL–3–dependent myeloid Leukemia cell lines," *Cell* 54:831–840 (1988).

Morishita et al., "Unique expression of the human Evi–1 gene in an endometrial carcinoma cell line: sequence of cDNAs and structure of alternatively spliced transcripts," *Oncogene* 5:963–971 (1990).

Piao et al., "Frequent frameshift mutations of RIZ in sporadic gastrointestinal and endometrial carcinomas with microsatellite instability," *Cancer Research* 60:4701–4704 (2000).

Roth et al., "p53 tumor suppressor gene therapy for cancer," *Oncology* 13(10):148–154 (1999).

Sakurada et al., "RIZ, the retinoblastoma protein interacting zinc finger gene, is mutated in genetically unstable cancers of the pancreas, stomach, and colorectum," *Genes, Chromosomes & Cancer* 30(2):207–211 (2001).

Steele–Perkins et al., "Tumor formation and inactivation of RIZ1, an Rb–binding member of a nuclear protein–methyltransferase superfamily," *Genes and Development* 15(17):2250–2262 (2001).

Xie et al., "Transcriptional reppression mediated by the PR domain zinc finger gene RIZ," *J. Biol. Chem.* 272:26360–26366 (1997).

Yamamoto et al., "Frameshift somatic mutations in gastrointestinal cancer of the microsatellite mutator phenotype," *Cancer Res.* 57:4420–4426 (1997).

* cited by examiner

```
hRIZ       SAPASMLPV TSSRFKRRTS SPPSSPQHSP ALRDFGKP D GKAAWTD QL TSKK KLES             779
rRIZ       SAPASMLPV TSSRFKRRTS SPPSSPQHSP ALRDFGKP D GKAAWTD VL TSKK KLES             773
Consensus  SAPASMLPV TSSRFKRRTS SPPSSPQHSP ALRDFGKP D GKAAWTD  L TSKK KLES             780 hRIZ       SDSPAWSLSC RDERET SPP CFDEYK SKE W ASS FSSV CNQQPLDLSS GVKQK ECTG           839
rRIZ       SDSPAWSLSC RDERET SPP CFDEYK SKE W ASS FSSV CNQQPLDLSS GVKQK ECTG           833
Consensus  SDSPAWSLSC RDERET SPP CFDEYK SKE W ASS FSSV CNQQPLDLSS GVKQK ECTG           840 hRIZ       KTPV WESVL DLSVHKK C  DSEGKEFKE  S QPTCE  KK KPTTCML QKVLLNEYNQ             899
rRIZ       KTPV WESVL DLSVHKK PC DSEGKEFKEN H LQP -- AA KPTTCML QKVLLNEYNQ             889
Consensus  KTPV WESVL DLSVHKK Q  DSEGKEFKE  H QP    A  KPTTCML QKVLLNEYNQ              900 hRIZ       I LP ENPAD TRSPSPCKS  LEAQPDP LG P SGFPAPTV ES HPM  PS SP CQT SLS           958
rRIZ       V LP E TPE TRSPSPCKS, PDTQPDP LG P SGCSV PT ES PW CPS PS SP LQT SLS         949
Consensus    LP E      TRSPSPCKS     QPDP LG P  S      PT ES  B M   PS SP  QT SLS     960 hRIZ       SGQLPPLL P T PSSPPPCP PVLTVATPPP PLLPTVPLPA PSSEASPH C PSP SNPTAQ            1018
rRIZ       SGQLPPLL P T PSSPPPCP PVLTVATPPP PLLPTVPLEH PSSEASPD C PSP SN TAQ            1009
Consensus  SGQLPPLL P T PSSPPPCP PVLTVATPPP PLLPTVPL    PSS ASP  C PSP SN  TAQ          1020 hRIZ       SPLPILSPTV SPSPSPIPPV EPLMSAASPG PPTLSSSSSS SSS SFSES SS SF PP               1078
rRIZ       SPLPILSPTV SPSPSPIPPV EPLMSAASPG PPTLSSSSSS SSS SFSES S  SF P-               1067
Consensus  SPLPILSPTV SPSPSPIPPV EPLMSAASPG PPTLSSSSSS SSS  S S  S  S  P                1080
```

FIGURE 1C

```
hRIZ        LSA SSVVSS GDNLEASLR  ISFKQEE EN EGLKP EEPQ   AA   VVQ ETF KNF CN    1138
rRIZ        LSA SSVVSS GDNLEASLR  VTFKQEE GS EGLKP EEAP   A    VVQ ETF KNF CN    1126
Consensus   LSA SSVVSS GDNLEASLR      FKQEE    EGLKP EE   A    VVQ ETF KNF CN    1140 hRIZ        VCESPFLSIK DLTKHLS HA EEWPFKCEFC VQLFK KTDL SEHRFLLHGV GNIFVCSVCK    1198
rRIZ        VCESPFLSIK DLTKHLS HA EEWPFKCEFC VQLFK KTDL SEHRFLLHGV GNIFVCSVCK    1186
Consensus   VCESPFLSIK DLTKHLS HA EEWPFKCEFC VQLFK KTDL SEHRFLLHGV GNIFVCSVCK    1200 hRIZ        KEFAFLCNLQ QHQRDLHPC  VCTHDIEFESG TLRPQNFTDP SKA VEHD S LPE PLETSK   1258
rRIZ        KEFAFLCNLQ QHQRDLHPD  VCTHBIEFESG TLRPQNFTDP SKA VEHD S LPE PLETSR   1246
Consensus   KEFAFLCNLQ QHQRDLHPD  VCTHHEFESG TLRPQNFTDP SKA VEHD S LPE PLETS     1260 hRIZ        EEE LNDSSE ELYTTIKIMA SGIKTKDPDV RLGLNQHYPS FKPPPFQYHH RNPMGIGVTA    1318
rRIZ        EEE LNDSSE ELYTTIKIMA SGIKTKDPDV RLGLNQHYPS FKPPPFQYHH RNPMGIGVTA    1305
Consensus   EEE LNDSSE ELYTTIKIMA SGIKTKDPDV RLGLNQHYPS FKPPPFQYHH RNPMGIGVTA    1320 hRIZ        TNFTTHNIPQ TFTTAIRCTK CGKGVDNMPE LHKHILACAS ASDKKRYTPK KNPVPLKQTV    1378
rRIZ        TNFTTHNIPQ TFTTAIRCTK CGKGVDNMPE LHKHILACAS ASDKKRYTPK KNPVPLKQTV    1365
Consensus   TNFTTHNIPQ TFTTAIRCTK CGKGVDNMPE LHKHILACAS ASDKKRYTPK KNPVPLKQTV    1380 hRIZ        QPKNGVVVLD NSGKNAFRRM GQPKRI  FV  EL EKMS NKL KL ALKKKNQ LVQKAILQKN   1438
rRIZ        QPKNGVVVLD NSGKNAFRRM GQPKRL  FV  EL KMS  NKL KL ALKKKNQ LVQKAILQKN   1425
Consensus   QPKNGVVVLD NSGKNAFRRM GQPKRL  FV  EL KMS  NKL KL ALKKKNQ LVQKAILQKN   1440
```

FIGURE 1D

```
hRIZ       KSAKQKADLK NAQESSHIC PYC REFTYI GSLNKHAAFS CPKKPLSPK  KVSHSSKKQ   1498
rRIZ       RAAKQKADLR DTEESSHIC PYC REFTYI GSLNKHAAFS CPKKPLSPK  KVSHSSKKQ   1485
Consensus       AKQKADL    SSHIC PYC REFTYI GSLNKHAAFS CPKKPLSP K  KVSHSSKKQ  1500 hRIZ       CHSPASSDK NSNSNHRRRT ADEIKMQSM QI PLGKTRAR SFCRIQ VLP SSSFRS QNV   1558
rRIZ       CHSSESSDR NSSCHRRRT ADEIKMQST QI PLGKTRAR SHCPAQ SLP SSSFRS QNV   1545
Consensus      SSD     NS    RRRT A  EIKMQS  Q  PLGKTRAR S  Q   LP SSSFRS QNV  1560 hRIZ       KFAASVKSKK HSSSSLRNSS PIRMAKITHV EGKKPKAVAK HSAQLSSKT SRELHVRVQK   1618
rRIZ       KFAASVKSKK HSSSSLRNSS PIRMAKITHV EGKKPKAVAK HSAQLSSKS SR LHVRVQK   1605
Consensus  KFAASVKSKK  SSSSLRNSS PIRMAKITHV EGKKPKAVAK HSAQLSSK  SR LHVRVQK   1620 hRIZ       SKAVIQSKFT LASKRTDRF NIKSRERSGG PITRSLQLAA AADLSENKRE DISAKQELKD   1678
rRIZ       SKAVIQSKTA LASKRTDRF TVKSRERSGG PITRSLQLAA AADLSESFRE DESARELKD   1665
Consensus  SKAV QSK   LASK RTDRF   KSRERSGG P TRSLQLAA AADLSE     E D SA ELKD  1680 hRIZ       FSYSLRLASR CSPPAAYIT RQTRKVKAHA AQFQGPFTK E                        1719
rRIZ       FSYSLRLASR CSSTAFYIT RQ RKVKAHA ADHFQGPFTK EX                      1707
Consensus  FSYSLRLASR C     A YIT RQ RKVKA A A  FQGPF K E                    1722
```

METHODS OF DETECTING AND TREATING MICROSATELLITE-INSTABILITY POSITIVE TUMORS USING RIZ

This application claims the benefit of U.S. Provisional Application No. 60/256,582, filed Dec. 19, 2000, which is incorporated herein by reference.

This invention was made in part with U.S. Government support under Grant No. RO1-CA76146 awarded by the National Institutes of Health. The U.S. Government has certain rights in this invention.

BACKGROUND OF THE INVENTION

1. Field of the Invention

The invention relates to the field of cancer and, more specifically, to methods for detecting and treating microsatellite-instability positive (MSI(+)) tumors using the RIZ tumor suppressor gene.

2. Background Information

The retinoblastoma protein (Rb)-interacting zinc finger gene (RIZ) is a candidate tumor suppressor gene belonging to the PR (PRDI-BFl-RIZl homology) or SET (Suvar3-9, Enhancer-of-zeste, Trithorax) domain family of chromosomal regulators involved in chromatin-mediated gene activation and silencing. The PR/SET domain family plays an important role in human cancers as evidenced by genetic alterations of several members of this family. The PR domain of RIZ appears to be a protein-binding interface and can interact with a motif present in the C-terminal region of RIZ.

RIZ gene normally produces two protein products, RIZl and RIZ2, that differ at the N-terminal region by the presence or absence of the PR domain. The RIZl (PR+) product is considered a strong candidate for the tumor suppressor gene present on chromosomal region 1p36, a region commonly deleted in more than a dozen different types of human cancers. RIZl gene expression, but not RIZ2 expression, is commonly silenced in a variety of human tumors and tumor-derived cells, including those of breast, liver, colon, and neuroendocrine tissues (He et al., *Cancer Res.* 58:4238–4244 (1998); Jiang et al., *Int. J. Cancer* 83:541–547 (1999)). These tumors were characterized by inactivation of RIZ gene expression, rather than by mutation leading to altered RIZ protein structure. Forced RIZ1 gene expression in such tumor cells has been shown to cause G2/M cell cycle arrest, apoptosis, or both. However, the effect of RIZ1 expression in tumors in vivo has not been determined.

It is now commonly believed that cancers result from the accumulation of genetic alterations in cellular cancer-causing genes. These alterations are thought to be driven by genetic instabilities. Two major genetic instability pathways have been recognized in cancers, chromosomal instability (CIN) and microsatellite instability (MSI). The hallmarks of tumors of the CIN pathway are aneuploidy and loss of heterozygosity. In contrast, tumors of the MSI pathway are usually diploid and show massive instability in simple repeated sequences, or microsatellites.

Microsatellite instability is considered to result from defects in cells' DNA mismatch repair system. This system normally recognizes and restores misincorporated bases or slippage errors that occur during DNA replication. Loss of mismatch repair thus enhances the evolutionary process of mutagenesis and selection which underlies the development of cancer. The mechanism of tumorigenesis of MSI(+) tumors is thought to involve frameshift mutations of microsatellite repeats within coding regions of affected target genes whose inactivation directly contributes to tumor development.

In addition to mutation avoidance, DNA mismatch repair also plays a crucial role in determining the toxicity of a number of DNA-damaging agents that are used in cancer chemotherapy. For example, cell killing by methylating agents, such as N-methyl-N'-nitro-N-nitroguanidine, N-methyl-N-nitrosourea, streptozocin, temozolomide, and dacarbazine; by platinating agents, such as cisplatin and carboplatin; base analog drugs, such as 6-thioguanine; and other chemotherapeutic agents such as busulfan, etoposide and doxorubin, appears to require a functional mismatch repair system. Therefore, administration of chemotherapeutic drugs to patients with MSI(+) tumors may be ineffective.

Gene therapy with tumor suppressor genes is a simpler and less toxic alternative than chemotherapy or radiation. Several clinical trials are underway or proposed in which the tumor suppressor genes p53 or Rb are introduced into tumors which carry mutations in these genes, either using retroviral or adenoviral vectors (see, for example, Roth et al., *Oncology* 13S5:148–153 (1999). However, MSI(+) tumors generally do not carry mutations in p53 or Rb, and thus gene therapy with these genes is unlikely to be effective. To date, effective gene therapy methods for treating MSI(+) tumors have not been developed.

Accordingly, there exists a need to develop gene therapy approaches to treat MSI(+) tumors, and to develop reliable markers for determining the MSI status of tumors. The present invention satisfies this need and provides related advantages as well.

SUMMARY OF THE INVENTION

The invention provides a method of inhibiting growth of a microsatellite instability (MSI)-positive tumor. The method is practiced by introducing into an MSI-positive tumor a nucleic acid molecule encoding a RIZ1 polypeptide, and expressing the RIZ1 polypeptide in the tumor in an effective amount to inhibit growth of the tumor.

Also provided is a method of determining the MSI status of a tumor. The method is practiced by determining in the tumor the number of adenosine (A) nucleotides in a poly(A) tract of a RIZ nucleic acid molecule in the tumor. An abnormal number of adenosine nucleotides in the RIZ poly(A) tract indicates that the tumor is MSI-positive.

BRIEF DESCRIPTION OF THE DRAWINGS

FIGS. 1A–1E show a comparison of the complete human RIZ amino acid sequence (indicated as hRIZ; SEQ ID NO:4) with the complete rat RIZ amino acid sequence (indicated as rRIZ; SEQ ID NO:2). A consensus sequence is shown. Single letter amino acid symbols are used. Amino acids that are identical in hRIZ and rRIZ are shown as ".".

DETAILED DESCRIPTION OF THE INVENTION

Figure 2:
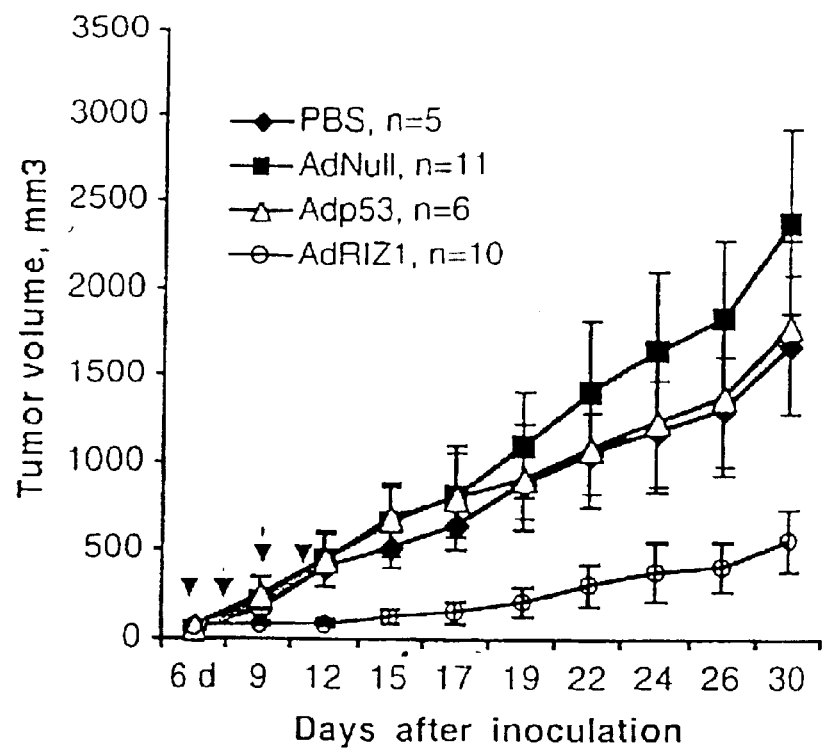
FIG. 2 shows the effect of intratumoral or peritumoral injections of either buffer, control Adnull adenovirus, Adp53 adenovirus, or AdRlZl adenovirus on tumor volume of established MSI(+) HCT116 colorectal cell tumors. Arrows indicated the time points when injections were administered.

The present invention provides a method of inhibiting growth of an MSI-positive tumor, comprising introducing into the tumor a nucleic acid molecule encoding a functional RIZ1 polypeptide, and expressing the polypeptide in the tumor in an effective amount to inhibit growth of the tumor. As disclosed herein, RIZ1 polypeptide is able to inhibit growth of MSI(+) tumor cells in vitro and MSI(+) tumors in vivo. In MSI(+) tumor cells that contain RIZ poly(A) tract frameshift mutations, RIZ1 polypeptide is also able to induce apoptotic cell killing both in vitro and in vivo.

As used herein, the term "microsatellite instability positive tumor cell" or "MSI-positive tumor cell" refers to a tumor cell that exhibits alterations in length of at least 20% of microsatellite marker sequences, in comparison with normal cells from the same individual. Preferably, an MSI-positive (MSI(+)) tumor cell exhibits alterations in at least 40% of microsatellite marker sequences tested, and more preferably at least 60% of microsatellite marker sequences tested, based on determination of alterations in at least five marker sequences. Preferably, an MSI(+) tumor will be determined to contain a frameshift mutation in a poly(A) tract of RIZ. However, due to the unexpectedly high frequency of such mutations in MSI(+) tumors, it is not necessary to predetermine whether RIZ contains mutations to expect to achieve a beneficial effect in a substantial percentage of treated individuals.

Microsatellite sequences are simple-sequence repeats of mono-, di-, tri- or tetra-nucleotides that occur throughout the genome. Panels of microsatellite marker sequences that are considered indicative of MSI status are known in the art (see, for example, Boland et al., Cancer Res. 58:5248–5257 (1998), and primers for analyzing microsatellite sequences are available commercially. Exemplary microsatellite marker sequences include the 5-marker panel of markers consisting of the mononucleotide repeat sequence markers BAT25 (GenBank accession no. 9834508) and BAT26 (GenBank accession no. 9834505); and the dinucleotide repeat sequence markers D5S346 (GenBank accession no. 181171), D2S123 (GenBank accession no. 187953) and D17S250 (GenBank accession no. 177030), proposed in Boland et al., supra (1998). Other suitable microsatellite marker sequences are described, for example, in Boland et al., supra (1998), and Mao et al., Proc. Natl. Acad. Sci. USA 91:9871–9875 (1994).

Microsatellite instability (MSI) is associated with a significant percentage of a variety of sporadic and hereditary tumor types. The methods of the invention are useful in inhibiting growth, and determining MSI status, of both sporadic and hereditary MSI(+) tumors.

In particular, MSI has been found in tumors of the head and neck (e.g. poorly differentiated head and neck tumors), thyroid, esophagus, stomach, colon, prostate (e.g. poorly differentiated prostate tumors), ovary, endometrium (e.g. poorly differentiated endometrial tumors), cervix, breast, melanoma (e.g. metastatic melanoma), small cell lung carcinoma, non small cell lung carcinoma, chronic myelogenous leukemia (e.g. blast crisis), and follicle center cell lymphoma (reviewed in Claij et al., Exp. Cell Res. 246:1–10 (1999)).

The majority of tumors associated with hereditary non-polyposis colon carcinoma (HNPCC) exhibit microsatellite instability. HNPCC is a familial cancer predisposition syndrome that accounts for about 10% of the total incidence of colorectal cancer. HNPCC is characterized by an early onset of colon cancer, often accompanied by other primary cancers of the colon, endometrium, ovary, small bowel, stomach, urinary tract, sebaceous glands and skin. The methods of the invention are particularly useful in inhibiting growth, and determining MSI status, of HNPCC tumors.

As used herein, the term "tumor" refers to a localized growth of cancer cells, which can be the site where a cancer originally formed or can be a metastatic lesion. The term "tumor cell" refers to a malignant cell, either within a tumor or metastatic lesion, or isolated from a tumor or metastatic lesion. A tumor cell isolated from a tumor or metastatic lesion can optionally be cultured for one or several generations.

As used herein, the term "inhibits growth of a tumor," refers to any slowing of the rate of tumor cell proliferation, arrest of tumor cell proliferation, or killing of cells within the tumor, such that the rate of tumor growth is reduced in comparison with the observed or predicted rate of growth of an untreated control tumor. The term "inhibits growth" can also refer to a reduction in size or disappearance of the tumor, as well as to a reduction in its metastatic potential. Those skilled in the art can readily determine, by any of a variety of suitable indicia, whether tumor growth is inhibited.

Inhibition of tumor growth can be evidenced, for example, by arrest of tumor cells in a particular phase of the cell cycle. For example, as described in Example I, below, exogenous RIZ1 expression causes arrest at the G2/M phase of the cell cycle in MSI(+) tumor cells, whether or not they contain RIZ poly(A) tract frameshift mutations.

Inhibition of tumor growth can also be evidenced by direct or indirect measurement of tumor size. For example, as described in Example III, below, exogenous RIZ1 expression causes a reduction in the rate of increase in volume of MSI(+) tumors. In human cancer patients, such measurements generally are made using well known imaging methods such as magnetic resonance imaging, computerized axial tomography and X-rays. Tumor cell growth can also be determined indirectly, such as by determining the levels of circulating carcinoembryonic antigen (CEA), prostate specific antigen or other tumor-specific antigens that are correlated with tumor growth. Inhibition of tumor growth is also generally correlated with prolonged survival and/or increased health and well-being of the subject.

As described in Examples I and III, below, expression of exogenous RIZ1 in MSI(+) tumor cell lines and tumors, particularly MSI(+) tumors with RIZ poly(A) tract frameshift mutations, also can induce apoptosis. As used herein, the term "induces apoptosis" refers to the promotion of a form of programmed cell death characterized by DNA fragmentation. Apoptosis can be determined by methods known in the art. For example, as described in Example III, below, kits are commercially available that detect the presence of fragmented DNA by in situ immunohistochemistry (e.g. Apoptag, available from Intergen, Purchase, N.Y.). Additionally, as described in Example I, below, apoptosis can also be determined by FACS analysis, in which apoptotic cells exhibit a sub-G1 DNA content, indicating DNA fragmentation.

The invention method is practiced by introducing into an MSI(+) tumor a nucleic acid molecule encoding a RIZ1 polypeptide, and expressing RIZ1 in an effective amount in the tumor. As used herein, the term "RIZ1 polypeptide" refers to a polypeptide having the human RIZ1 amino acid sequence designated SEQ ID NO:4, or to a functional fragment thereof. The term "RIZ1 polypeptide" also refers to a polypeptide having one or more minor modifications to the sequence designated SEQ ID NO:4, so long as the polypeptide retains the ability to inhibit growth of an MSI(+) tumor or tumor cell. Minor modifications include one or more additions, deletions or substitutions to the sequence of SEQ ID NO:4, that do not deleteriously affect its growth-inhibitory ability.

The cloning of the human RIZ gene designated SEQ ID NO:3, which encodes a RIZ1 polypeptide having the amino acid sequence designated SEQ ID NO:4, as well as the cloning of the rat RIZ gene designated SEQ ID NO:1 (which encodes SEQ ID NO:2), and the mouse RIZ gene designated SEQ ID NO:8 are described in U.S. Pat. Nos. 6,069,231, 5,831,008 and 5,811,304, and in Buyse et al., *Proc. Natl. Acad. Sci. USA* 92:4467–4471 (1995).

Figure 1A:
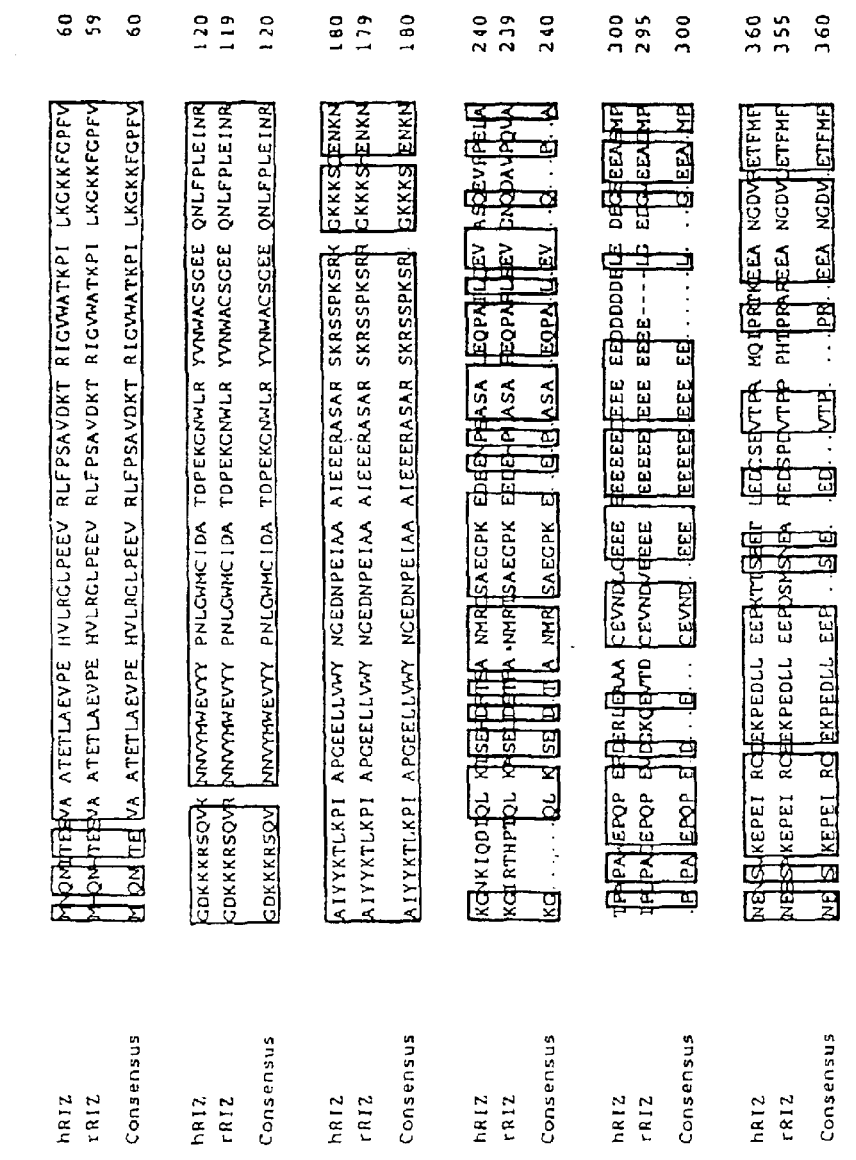
Figure 1B:
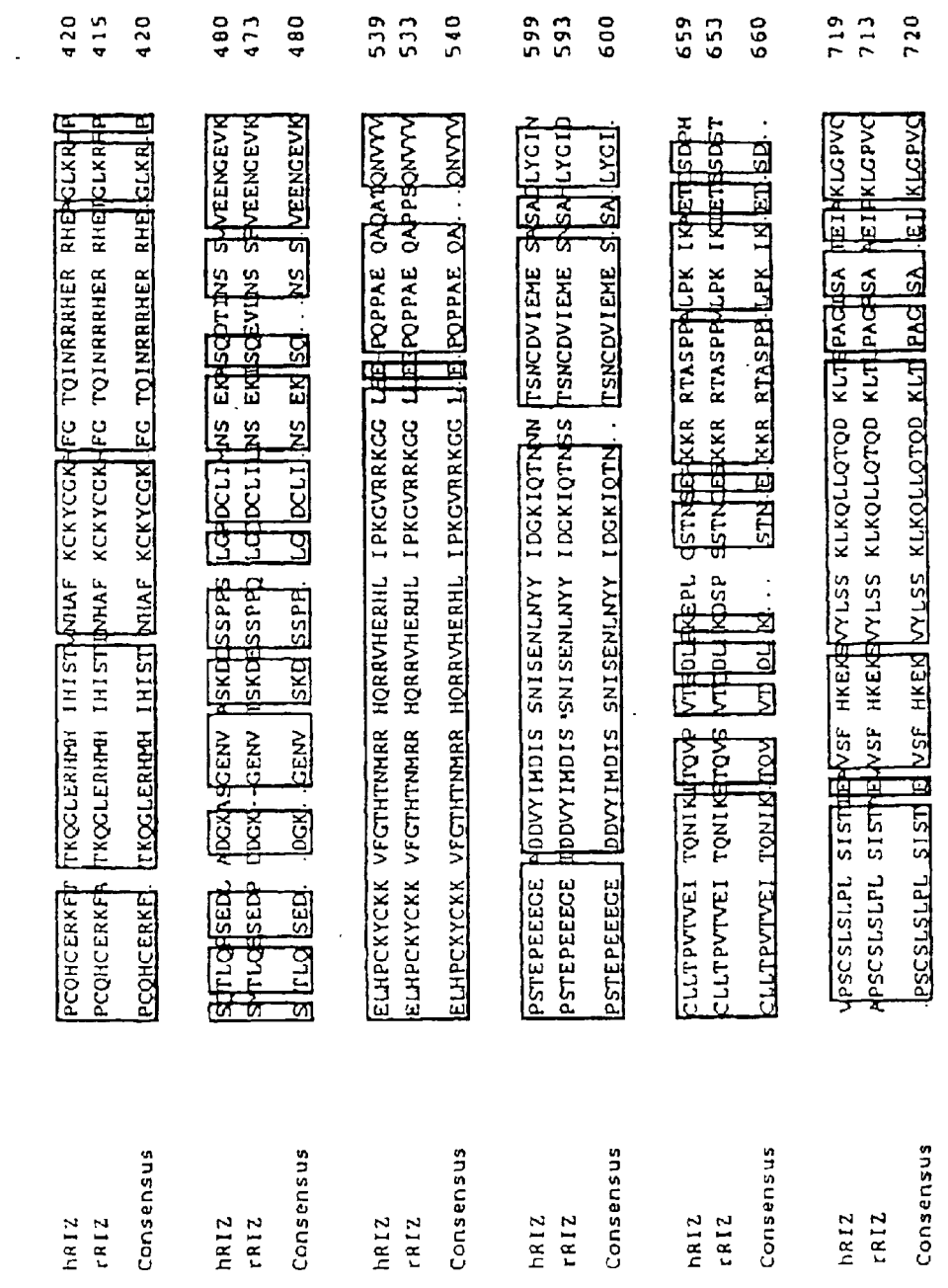

A RIZ1 polypeptide can have at least 70% identity to the amino acid sequence designated SEQ ID NO:4. Preferably, a RIZ1 polypeptide will have at least 75% identity, including at least 80%, 85%, 90%, 95%, 98%, 99% or greater identity to SEQ ID NO:4. For example, a RIZ1 polypeptide can be a RIZ1 from another mammalian species. As shown in FIG. 1, human RIZ1 (SEQ ID NO:4) and rat RIZ1 (SEQ ID NO:2) are 84% identical over their sequences.

It is well known in the art that evolutionarily conserved amino acid residues and domains are more likely to be important for maintaining biological activity than less well-conserved residues and domains. Thus, it would be expected that substituting a residue that is highly conserved among RIZ polypeptides across species, with a non-conserved residue may be deleterious, whereas making the same substitution at a residue which varies widely among species would likely not have a significant effect on biological activity.

Substitutions to the amino acid sequence designated SEQ ID NO:2 can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Additions to a RIZ polypeptide include, but are not limited to, the addition of "tag" sequences at the N or C termini, or between domains. Such tag sequence include, for example, epitope tags, histidine tags, glutathione-S-transferase (GST), and the like, or sorting sequences. Such additional sequences can be used, for example, to facilitate expression or identification of a recombinant RIZ1.

Exemplary modifications to the RIZ1 polypeptide sequence designated SEQ ID NO:4 include normal allelic variants of SEQ ID NO:4, such as RIZ1 in which the first three amino acids by the amino acid sequence designated SEQ ID NOS:6 or 7. Another exemplary allelic variant contains a single nucleotide change of $T_{969}$ to $A_{969}$, leading to a change of amino acid residue $D_{283}$ to $E_{283}$. The $T_{969}$ allele is estimated to be two times more frequent than the $A_{969}$ allele. A further allelic variant of SEQ ID NO:4 is a variant in which the proline at residue 704 is deleted.

In one embodiment, a RIZ1 polypeptide expressed in a tumor in a method of the invention comprises the PR domain of SEQ ID NO:4, designated SEQ ID NO:5, or a sequence at least 95% identical thereto, such as the PR domain of rat RIZ.

RIZ1 contains a region of about 100 residues near the N-terminus that is designated the "PR domain" because it is 42% homologous with a similar N-terminal region from PRDI-BF1 and Blimp-1. The PR domain is also homologous to an N-terminal portion of the mammalian Evi-1 protein (Morishita et al., *Cell* 54:831–840 (1988); Morishita et al. *Oncogene* 5:936–971 (1990)) and to an N-terminal portion of the *C. elegans* egl-43 protein, which is a homolog of Evi-1 (Garriga et al., *Genes Devel.* 7:2097–2109 (1993)).

The PR domain has been demonstrated to be required for the negative regulatory function of RIZ (He et al., *Cancer Res.* 58:4238–4244 (1998)), and may be involved in chromatin-mediated transcriptional activation or repression (Xie et al., *J. Biol. Chem.* 272:26360–26366 (1997); Huang et al., *J. Biol. Chem.* 273:15933–15939 (1998)).

In general, a PR domain is about 100 to about 120 amino acids in length and contains three highly conserved sequences, designated blocks A, B and C, which consist of about 10 to about 12 amino acids, separated by less conserved sequences of about 20 to about 35 amino acids. Each of blocks A, B and C is encoded by an individual exon. The PR domains of rat RIZ (a.a. positions 36 to 151 of SEQ ID NO:2) and human RIZ (a.a. positions 37 to 152 of SEQ ID NO:4; designated SEQ ID NO:5) are identical except that the human RIZ contains a lysine at a.a. position 70, whereas the rat RIZ contains an arginine at the equivalent position (a.a. position 69). Additionally, analysis of a cDNA encoding a portion of the mouse RIZ protein that includes blocks B and C of a PR domain peptide (SEQ ID NOS:8 and 9) revealed that the deduced amino acid sequence (i.e. the first 75 amino acids of SEQ ID NO:9) is identical to the corresponding region of the PR domain in human RIZ (i.e. amino acids designated as positions 42–116 of human RIZ SEQ ID NO:5).

The RIZ1 polypeptide includes several other motifs of interest, including an RB-binding motif related to that of the E1A oncoprotein; eight zinc finger motifs; and a C-terminal PR-binding motif. The interaction of the N-terminal PR domain with the C-terminal PR binding domain may be necessary for homo- or hetero-oligomerization of RIZ, and for interactions with other proteins.

Those skilled in the art can readily determine, by the methods disclosed herein, whether a RIZ1 polypeptide that is a modification or fragment of SEQ ID NO:4 retains the ability to inhibit growth of an MSI(+) tumor or tumor cell. As disclosed in Examples I and III, the ability of a RIZ1 polypeptide to inhibit MSI(+) tumor cell growth in vitro is predictive of its ability to inhibit MSI(+) tumor growth in vivo. Therefore, a nucleic acid molecule encoding a RIZ1 polypeptide that is a modification or fragment of SEQ ID NO:4 can be introduced either into an MSI(+) tumor, or into a tumor cell, such as an HCT116+ tumor cell line, to determine whether it retains the ability to inhibit growth. If so, the nucleic acid molecule is suitable for use in the methods of the invention.

A nucleic acid molecule encoding a RIZ1 polypeptide can be contained in any suitable vector for expression in a mammalian subject. Appropriate vectors include, but are not limited to, viral vectors such as retroviral vectors (e.g. replication-defective MuLV, HTLV, and HIV vectors); adenoviral vectors; adeno-associated viral vectors; herpes simplex viral vectors; and non-viral vectors (e.g. viral genomes, plasmids and phagemids) (see, for example, Kaplitt and Loewy, *Viral Vectors: Gene Therapy and Neuroscience Applications* Academic Press, San Diego, Calif. (1995); Chang, *Somatic Gene Therapy* CRC Press, Boca Raton, Fla.

(1995)). Methods of cloning nucleic acid molecules encoding any desired sequences are well known in the art.

Adenoviral vectors are particularly advantageous in that they can transduce both relicating and non-replicating cells, and can be grown to high titers in vitro. Additionally, adenoviral vectors do not integrate into the host genome, resulting in a safety advantage. Adenoviral vectors have been successfully used to introduce the p53 tumor suppressor gene into tumors, with low toxicity, high levels of gene expression, and therapeutic efficacy (e.g. Swisher et al., *J. Natl. Cancer Inst.* 91:763–771 (1999); Clayman, Seminars in Oncology 27S8:39–43 (2000)).

Optionally, a viral vector or other vector can be constructed to express a nucleic acid encoding a RIZ in a tissue specific manner by incorporating a tissue-specific promoter or enhancer into the vector (e.g. Dai et al., *Proc. Natl. Acad. Sci. USA* 89:10892–10895 (1992)). Alternatively, a nucleic acid molecule encoding a RIZ1 polypeptide need not be incorporated into a vector, so long as it is linked to appropriate nucleotide sequences required for transcription and translation.

Appropriate formulations for delivery of nucleic acid molecules can be determined by those skilled in the art, depending, for example, on the type of vector (e.g. infectious or non-infectious) and route of delivery. Suitable formulations include, for example, incorporating the nucleic acid molecules into liposomes; mixing the nucleic acid molecules with polycationic agents; and conjugating the nucleic acid molecules to targeting molecules (e.g. antibodies, ligands, lectins, fusogenic peptides, or HIV tat peptide). Gene therapy methods, including considerations for choice of appropriate vectors, promoters and formulations, are reviewed, for example, in Anderson, *Nature* 392:25–30 (1998).

A nucleic acid molecule encoding a RIZ1 polypeptide can be administered to a subject by various routes such that the polypeptide is expressed in an effective amount in the tumor. In a preferred embodiment, administration of the nucleic acid molecule is local, such as intra- or peri-tumoral, which can be achieved, for example, by injection or particle bombardment. Depending on the tumor location, local administration can optionally be performed in conjunction with a surgical procedure, or by using imaging procedures to direct a delivery instrument to the tumor site (e.g. Swisher et al., supra (1999)). Local administration can be advantageous is that there is no dilution effect and, therefore, the likelihood that a majority of the tumor cells will be contacted with the nucleic acid molecule is increased.

Administration of a nucleic acid molecule encoding RIZ1 can alternatively be systemic, such as via intravenous or intra-arterial injection, or via administration into a body compartment (e.g. intraperitoneal or intracerebral compartments). Systemic routes are particularly advantageous for treating disseminated tumors.

Receptor-mediated DNA delivery approaches can be advantageous when administering a nucleic acid molecule encoding a RIZ1 polypeptide at a site other than at the tumor site. For example, a viral particle can be complexed with a tissue-specific or tumor-specific ligand or antibody via a bridging molecule. Following administration, the viral particles will circulate until they recognize host cells with the appropriate target specificity for infection.

The invention also provides a method of determining MSI status of a tumor, comprising determining the number of adenosine (A) nucleotides in a poly(A) tract of a RIZ nucleic acid molecule in the tumor, wherein an abnormal number of adenosine nucleotides in the RIZ poly(A) tract indicates that the tumor is MSI-positive.

As disclosed herein, frameshift mutations in either of two poly-adenosine tracts of the RIZ gene were detected in a high percentage of MSI(+) tumor cells and cell lines, including tumors and cell lines derived from colon, gastric and endometrial tissue. In contrast, RIZ poly(A)-tract mutations were not detected in MSI– tumor cells and cell lines. Accordingly, the determination that a tumor contains a RIZ poly(A) tract frameshift mutation strongly predicts that the tumor is MSI(+).

Scanning of RIZ1 cDNA sequence revealed two potentially hypermutable polyadenosine tracts within its coding region in exon 8: one $(A)_8$ tract at residues 4393–4400 of SEQ ID NO:3, and one $(A)_9$ tract at residues 4582–4590 of SEQ ID NO:3. The $(A)_8$ tract of the RIZ gene is immediately 5' of the most C-terminal zinc finger domain, and frameshift mutation in this tract predicts termination of translation such that this zinc finger would be truncated. The $(A)_9$ tract is 30 nt (10aa) past this same zinc finger domain. Frameshift mutations in either tract, caused by an addition or deletion of an A residue, are predicted to lead to loss of the C-terminal domain of the RIZ protein that is involved in PR binding.

Methods of determining the number of A residues in a RIZ gene $(A)_8$ tract or $(A)_9$ tract are known in the art and include, for example, PCR amplification of RIZ genomic DNA, or RIZ cDNA, followed by SSCP analysis and/or direct sequencing of the region of interest. Exemplary methods of determining the number of A residues in a RIZ gene $(A)_8$ tract or $(A)_9$ tract are described in Examples I and II, below.

The DNA sample to be analyzed is preferably obtained directly from the tumor, such as by a tissue biopsy. Either fresh or fixed tissue sections can be assayed. For certain applications of the method, it may be preferable to analyze tumor cells released into the urine, blood or lymph, or tumor cells that have been passaged in culture.

As described previously, tumors that are MSI(+) may be less susceptible to certain types of chemotherapy than tumors that are MSI–. Therefore, it is important to be able to predict the MSI status of a tumor prior to initiating treatment, such that therapy can be optimized. As described herein, tumors that are MSI(+) are susceptible to growth inhibition and apoptosis by introduction and expression of exogenous RIZ1. Accordingly, RIZ gene therapy can be used as an alternative to chemotherapy, or in combination with other therapies.

The following examples are intended to illustrate but not limit the present invention.

EXAMPLE I

RIZ Mutations in MSI(+) Tumors, and Effect of Ectopic Expression of RIZ in MSI(+) Tumors This example shows that RIZ poly(A)-tract frameshift mutations are present in a high percentage of MSI(+) tumor cells of a variety of different cell types. This example also shows that expression of a nucleic acid molecule encoding functional RIZ in an MSI(+) tumor cell containing a RIZ poly(A)-tract frameshift mutation induces cell cycle arrest and apoptosis of the tumor cells.

Materials and Methods

Tissue Samples and Cell Lines. 22 MSI(–) tumors were studied. 8 of these were selected because they previously had been found to display a CIN (chromosomal instability) phenotype, including LOH at two closely linked markers, D1S228 [32.4 centimorgans (cM)] and D1S507 (36.2 cM) (Canzian et al., *Cancer Res.* 56:3331–3337 (1996)). In 14 tumors, the LOH status at 1p was unknown. Additionally, 3 MSI(−) lines were obtained from the American Type Culture Collection (ATCC). The MSI(−) lines were MDAMB231, MDAMB435S, and SKBR3 (breast cancer), which had been previously characterized for RIZ expression (He et al., *Cancer Res.* 58:4238–4244 (1998)).

In addition, 24 MSI(+) tumors from hereditary nonpolyposis colorectal cancer (HNPCC) patients were studied (Aaltonen et al., *N. Eng. J. Med.* 338:1481–1487 (1998)). Moreover, 11 MSI(+) were obtained from the ATCC. The MSI(+) lines were DLD1, LS411N, SW48, HCT116, LoVo, HCT15, and LS174T (colorectal cancer); MDAH2774 and SK-OV3 (ovarian cancer); AN3CA (endometrial cancer); and DU145 (prostate cancer).

Loss of heterozygosity (LOH) analysis. Primary normal/tumor pairs were investigated by using fluorescently labeled microsatellites. Primer sequences were obtained from the Genome Database. Amplifications of each microsatellite were done in 15 µl volumes with 10 ng of each respective genomic DNA, 8 pmol of each primer (5' primer, fluorescently labeled), 100 µM each dNTP, 0.6 unit of AmpliTaq Gold DNA Polymerase (PE Biosystems, Foster City, Calif.), 10 mM Tris.HCl (pH 8.3), 50 mM KCl, and 2 mM $MgCl_2$. PCR products were loaded onto a 377XL sequencer (PE Biosystems). Allele size and fluorescent intensity were determined by GENESCAN and GENOTYPER software (PE Biosystems). LOH was analyzed by determining the fluorescent intensity of each allele and calculating the ratio (Canzian et al., *Cancer Res.* 56:3331–3337 (1996)). A sample was scored as showing LOH if an allelic ratio of <0.67 or >1.5 was obtained.

Because of a high degree of MSI observed in the HNPCC tumor DNAs, single-nucleotide polymorphisms (SNPs) were also used to determine LOH in the subset of 24 HNPCC normal/tumor DNA pairs. Primer sequences were obtained from the human SNP database. SNPs were amplified in 25 µl volumes with 100 nmol of each of the respective PCR primers, 25 ng of genomic DNA, 100 µM each dNTP, 1.0 unit of AmpliTaq Gold DNA Polymerase (Perkin-Elmer), 10 mM Tris.HCl (pH 8.3), 50 mM KCl, and 2 mM $MgCl_2$. PCR products were purified by using exonuclease 1 and shrimp alkaline phosphatase (Amersham Life Sciences) and directly sequenced in one direction with one of the amplification primers and the BigDye Terminator chemistry (PE Biosystems). Samples that failed or sequenced poorly were resequenced in the other direction with the other amplification primer. LOH determination was done by a method similar to the microsatellite analysis.

Mutation Analysis. Candidate genes were screened for mutations by direct sequencing of genomic PCR products. To facilitate direct sequencing of PCR products, all primers were tailed with M13-forward (TGTAAAACGACGGCCAGT; SEQ ID NO:10) and M13-reverse (CAGGAAACAGCTATGACC; SEQ ID NO:11) sequences. PCRs were performed in 25-µl volumes with 100 nmol of each of the respective PCR primers, 25 ng of genomic DNA, 100 µM each dNTP, 1.0 unit of Taq Gold DNA polymerase (Perkin-Elmer), 10 mM Tris-HCl (pH 8.3), 50 mM KCl, and 2 mM MgCl2. PCR fragments were purified by using the Exonuclease I/Shrimp Alkaline Phosphatase PCR Product Presequencing Kit (United States Biochemical). After purification according to the manufacturer's protocol, 2 µl of the PCR products were sequenced by using the BigDye Terminator AmpliTaq FS Cycle Sequencing Kit (PE Biosystems).

Expression Analysis. RNA for expression analysis was isolated by using the RNAeasy Mini Kit (Qiagen, Chatsworth, Calif.). Reverse transcription of isolated RNA was done by using Superscript RT (Life Technologies, Rockville, Md.), and cDNA amplification was done by using the GeneAmp Gold RNA PCR kit (PE Biosystems). Primers used for determination of RIZ1- and RIZ2-specific PCRs were as described (He et al., supra (1998)). Glyceraldehyde-3-phosphate dehydrogenase (GAPDH)-specific primers were used as a control (Leygue et al., *Cancer Res.* 58:1348–1352 (1998)).

Immunoprecipitation and Immunoblot Analysis. Immunoprecipitation and immunoblot analysis was performed according to procedures described in Buyse et al., *Proc. Natl. Acad. Sci. USA* 92:4467–4471 (1995). Cell extracts were immunoprecipitated with RIZ antiserum 1637 against the N terminus of RIZ2, or preimmune serum. Immunoprecipitated products were resolved on a 5% SDS gel followed by immunoblot analysis using mouse antiserum KGSE against the N terminus of RIZ2.

Analysis of Cells Expressing Ectopically Introduced RIZ1. Analysis of cells expressing ectopically introduced RIZ1 was performed as described in He et al., supra (1998). Briefly, colon cancer cells were seeded at $2 \times 10^5$ cells in 6-cm dishes and infected with recombinant adenovirus at a multiplicity of infection of 100. At 48 hr postinfection, cells were processed for DNA histogram analysis.

Results

Deletion Mapping of 1p. Most of the sporadic colorectal cancer tumors showed deletion of the entire 1ptel region up to 40 cM, where there was a return to heterozygosity in several tumors (see FIG. 1 of Chadwick et al., *Proc. Natl. Acad. Sci. USA* 97:2662–2667 (2000)). The region of return to heterozygosity is telomeric to several candidate tumor suppressor genes and oncogenes, including PAX7 at 46.2 cM, PLA2 at 46.2 cM, E2F2 at 52.4 cM, and MYCL at 71 cM. In comparison with MSI(−) tumors, the area of shared deletion was more restricted in MSI(+) tumors from HNPCC patients. Although the majority of the SNP markers closest to 1ptel were not informative, a region of common deletion was identified by the marker WIAF-481 at 32.2 cM, which showed LOH in 8 of 15 (53%) informative HNPCC tumors. The allelic imbalance values for SNPs were highly reproducible, indicating the validity of these markers in the deletion mapping of MSI(+) tumors in particular. In comparison, a much lower rate of LOH was observed for nearby markers such as D1S450 (1/11) at 22.9 cM and D1S228 (1/8) at 32.4 cM.

Identification of RIZ as a Candidate Gene for 1p Alterations. Functional candidate genes in the region of 32.2 cM from 1ptel were examined and screened for mutations. The RIZ gene maps to 32.2 cM on GeneMap 99. RIZ is within 370 kb of D1S228, as inferred from yeast artificial chromosome analysis (Leygue et al., supra (1998)). RIZ lies in 3' to 5' orientation from the telomere of chromosome 1p. In HNPCC tumors, there was a gradual decline of the LOH rate from WIAF-481 to RIZ 3' to RIZ 5'. Three intragenic polymorphisms of RIZ were analyzed for LOH, including a codon Pro-704 deletion at exon 8, an intron 4 CA repeat, and a SNP flanking exon 4 (GAT to GAC 18 bases 3' of the coding exon 4 sequence). The LOH rates for these RIZ markers were 21% (3/14), 9% (1/11), and 0% (0/8), respectively. Tumor 5393T showed LOH of exon 8 Pro-704 but retention of the other intragenic markers, consistent with location of a deletion break point inside the RIZ gene. Analysis of MSI(−) tumors that were not preselected for 1p LOH revealed LOH rates of 30% (4/13), 23% (3/13), and 60% (3/5), respectively. Tumor 7T-OSU showed LOH of RIZP704 but retention of heterozygosity of RIZ intron 4 CA, again indicating a deletion breakpoint within RIZ. The location of RIZ in the vicinity of the common LOH region and the observed deletion breakpoints within RIZ suggest that RIZ is a candidate target of 1p36 alterations in both hereditary and sporadic colorectal cancers.

Examination of the coding sequence of RIZ showed potentially hypermutable tracts of $(A)_8$ and $(A)_9$ in exon 8 of the RIZ gene. In 9 of 24 (37.5%) of the MSI(+) HNPCC tumors, frameshift mutations were found in either the $(A)_8$ [one MSI(+) tumor] or the $(A)_9$ [eight MSI(+) tumors] tract. Furthermore, 6 of 11 MSI(+) cell lines (HCT116, LoVo, LS411N, LS174T, MDAH2774, and AN3CA) showed frameshift mutations in the $(A)_9$ tract. In cell lines HCT116 and AN3CA, the mutation was homozygous/hemizygous, resulting in biallelic involvement. None of the 23 tested MSI(−) sporadic colorectal cancers contained mutations in either of the polyadenosine tracts, indicating that these regions were mutational hotspots in MSI(+) tumors only.

RIZ Frameshift Mutations Are Clonally Selected in Tumorigenesis. To investigate whether similar mononucleotide tracts in other genes are involved to a comparable degree, the coding $(A)_8$ tracts of the PMS2 and DNA polymerase genes were analyzed. Frameshift mutations in these tracts were completely absent in the MSI(+) tumors (P=0.0005). MSI(+) tumors were further screened for mutations in the $(A)_9$ tracts of the RECQL, BLM, and KIAA0355 genes. One of 24 MSI(+) tumors had 1-bp deletions in the RECQL and KIAA0355 genes (P=0.005). MSI(+) tumors were screened further for mutations in the $(A)_9$ tracts of the RECQL, BLM, and KIA0355 genes. Of 24 MSI(+) tumors, 1 had 1-bp deletions in the BLM gene (P=0.005). Taken together, these results suggest that the RIZ frameshift mutations were specifically selected during the clonal evolution of colorectal tumorigenesis.

Decreased RIZ1 Expression in Cell Lines. Previous reports have shown that RIZ is expressed in two alternative transcripts, RIZ1 and RIZ2 (He et al., supra (1998)). RIZ1 is commonly lost, whereas RIZ2 is present uniformly in several 1p36-linked cancer types (He et al., supra (1998); Jiang et al., *Int. J. Cancer* 83:541–547 (1999); Jiang et al., *Histol. Histopathol.* 15:109–117 (2000)). To determine whether expression was affected in RIZ-mutated colorectal tumors, expression by the reverse transcription-PCR was examined as described in He et al., supra (1998); Jiang et al., supra (1999); and Jiang et al., supra (2000). Because of total overlap between the smaller RIZ2 and the larger RIZ1 transcripts, transcription was not measured for RIZ2 alone; hence, one reaction is specific for RIZ1, whereas the other measures RIZ1+RIZ2. Breast cancer cell line MDAMB435S was used as a control that expresses only the RIZ2 isoform, and MDAMB231 was used as a control cell line that expresses both RIZ1 and RIZ2 isoforms (He et al., supra (1998)).

MSI(+) colorectal cancer cell lines (4 of 11) showed reduced or lost mRNA expression of RIZ1 in the presence of abundant RIZ1+RIZ2 transcript, supporting observations that an imbalance in the amounts of RIZ1 and RIZ2 is associated significantly with malignancy (He et al., supra (1998); Jiang et al., supra (1999); and Jiang et al., supra (2000)). In three cell lines with altered RIZ1 expression, frameshift mutations in the polyadenosine tracts were present, including cell line HCT116, which is homozygous or hemizygous for this mutation. Of these cell lines, LS411N was found to express only the RIZ2 isoform, whereas LoVo showed reduced expression of RIZ1. Also, SW48 showed reduced or absent expression of RIZ1, but had no mutations in the adenosine repeats of RIZ. The RIZ sequence is large (nearly 8 kb), and it is possible that there are other areas in the gene or in the promoter region that could be affected, resulting in altered RIZ expression in these cell lines.

RNA isolated from frozen tissue from the mutation-positive HNPCC tumors did not show clear expression changes of RIZ. This finding is likely caused by the contamination of normal tissue in the isolated RNA tumor samples. Titration experiments of cell-line RNA showed that even with a mixture of 90% RIZ2-expressing mRNA to 10% RIZ1- and RIZ2-expressing mRNA, the RIZ1 and RIZ2 isoform is PCR amplified.

Frameshift Mutation Leads to Expression of Truncated RIZ Proteins. The frameshift caused by the deletion of one adenosine at the $(A)_9$ tract (at nucleotide position 4700 of the RIZ1 coding sequence) is expected to cause the fusion of truncated RIZ1 and RIZ2 lacking the C-terminal 219 aa with a novel reading frame of 76 aa. This would lead to the expression of mutant RIZ1 and RIZ2 that are 157 residues shorter than their wild-type counterparts. To confirm that such truncated RIZ1 and RIZ2 proteins indeed were expressed from the mutant allele, immunoprecipitation and immunoblot analysis was performed using the HCT116 cell line that is homozygous or hemizygous for the frameshift mutation. The usual pattern of RIZ protein expression in DLD1 cells that expressed both RIZ1 and RIZ2 mRNAs was first confirmed. In all tumor cell lines studied previously, RIZ1 protein was at low levels and difficult to detect, whereas RIZ2 protein was at higher levels and readily detectable (He et al., supra (1998); Buyse et al. supra (1995); Liu et al., *J. Biol. Chem.* 272:2984–2991 (1997)). Similarly, in DLD1 cells, RIZ2 protein of 250 kDa was detected, and RIZ1 protein was at low or undetectable levels. In contrast, full-length RIZ2 protein was not detected in the HCT116 cell line, but instead a shorter protein of 230 kDa was observed, consistent with truncation of RIZ2 protein by the frameshift mutation. Although the experiment was not informative for RIZ1 protein, a truncated RIZ1 protein could be inferred from the results on RIZ2.

RIZ1 Causes G2/M Arrest, Apoptosis, or Both in Colorectal Cancer Cell Lines. Adenovirus-mediated RIZ1 expression has been shown to cause G2/M arrest, apoptosis, or both in breast and liver cancer cell lines, which were not MSI(+). The effects of adenovirus-mediated RIZ1 expression on HCT116 and DLD1 colon cancer cell lines were examined. Immunoblot analysis confirmed full-length RIZ1 protein expression in both cell lines upon infection with AdRIZ1 at a multiplicity of infection of 100. The fraction of infected cells in G2/M increased significantly at 48 h after AdRIZ1 infection in HCT116 and DLD1 cells. At 48 and 72 h postinfection with AdRIZ1, HCT116 cells showed sub-G1 DNA content indicating apoptotic cell death (Table 1). However, few cells with sub-G1 DNA content were observed in DLD1. The results show that RIZ1 caused G2/M arrest and apoptosis in HCT116 cells, but only G2/M arrest in DLD1 cells.

TABLE 1

| Cell Line | Apoptosis | G1 | S | G2/M |
| --- | --- | --- | --- | --- |
| HCT116 | +25 ± 2.0 | −47 ± 1.3 | +6.1 ± 0.7 | +20 ± 0.8 |
| DLD1 | +9.5 ± 1.2 | −28 ± 2.1 | −2.2 ± 0.5 | +26 ± 1.7 |

In Table 1, DNA histogram analysis was performed 72 h after adenovirus (Ad) RIZ1 or AdNull virus infection. The values shown represent the difference in percentage of cell populations between AdRIZ1- and AdNull-infected cells. The increase caused by AdRIZ1 over AdNull is indicated by a plus sign (+) and a decrease is indicated by a minus sign (−). The values represent the mean±SD of three experiments.

The results described above indicate that the function of RIZ in tumors may be impaired by somatic events in at least two different ways. In MSI(+) tumors, frameshift mutations in the 3' end of the gene interfere with the interaction between the C terminus of the protein and its N-terminal PR domain. In MSI(−) tumors (CIN pathway), mutations or deletions of the PR domain of RIZ1 may have similar effects. In the series of tumors examined, RIZ was affected by either LOH or frameshift mutation, but not both, suggesting that LOH and frameshift mutations have similar, alternative functions in RIZ-associated tumorigenesis.

EXAMPLE II

RIZ Poly(A)-Tract Frameshift Mutations in MSI(+) Gastric Cancers

This example shows that RIZ poly(A)-tract frameshift mutations occur with high frequency in MSI(+) gastric cancers.

To examine the role of RIZ in MSI(+) tumors, a total of 179 primary gastrointestinal and endometrial tumors from patients undergoing surgery were analyzed. Among them, 109 tumors were characterized as MSI-High, including 40 gastric carcinomas (K), 18 endometrial cancers (E or AN), and 51 colorectal cancers (AC, IC or AS). MSI-High status in primary tumors was defined according to the criteria proposed by Boland et al., supra (1998). The source of tumor samples is described in Kong et al., *Nat. Genet.* 17:143–144 (1997); Yamamoto et al., *Cancer Res.* 57:4420–4426 (1997); and Kim et al., *Lab. Investig.* 79:1113–1120 (1999). A panel of MSI(+) cell lines derived from colon (HCT116, SW-48, LOVO, LS441N, LS180, LS174T, DLD1, HCT15, HCT8), prostate (DU145), breast (Cal-51), and uterus (AN3CA, SK-UT-1B) cancers was also screened (obtained from ATCC). The MSI(−) colon cancer cell line SW620 was also included as a control.

Frameshift mutations at the $(A)_8$ and $(A)_9$ tracts in RIZ were detected by PCR with Vent DNA polymerase and SSCP analysis. The $(A)_8$ tract was amplified by PCR with primers RIZA8-F, 5'-GAGCTCAGCAAAATGTCGTC-3' (SEQ ID NO:12) and RIZA8-R, 5'-CAAGTCGGCCTTCTGCTTTG-3' (SEQ ID NO:13). The $(A)_9$ tract was amplified by PCR with primers RIZA9-F, 5'-TCTCACATCTGCCCTTACTG-3' (SEQ ID NO:14) and RIZA9-R, 5'-GTGATGAGTGTCCACCTTTC-3' (SEQ ID NO:15). PCR was carried out as described in Yamamoto et al., supra (1997). PCR was performed with primers RIZA8-F and RIZA9-R for SSCP analysis, as described in Yamamoto et al., supra (1997). The mutated bands in the SSCP gel were sequences using the Big Dye terminator cycle sequencing kit (Perkin-Elmer Corp.).

RIZ mutations were detected in 19 of 40 (48%) MSI(+) gastric carcinomas, 6 of 18 endometrial cancers (33%), 14 of 51 (26%) colorectal cancers, and 7 of 13 (54%) of MSI(+) cell lines examined (HCT116, LOVO, LS441N, LS180, LS174T, HCT8, and AN3CA). These mutations were somatic because the corresponding normal counterparts were wild type. With the exception of a mutation in the $(A)_8$ tract in KS19 (gastric carcinoma), E75 (endometrial cancer), AC334 (colon cancer) and AC590 (colon cancer), all mutations targeted the $(A)_9$ tract. No RIZ mutations were found in 70 MSI(−) gastric carcinomas, indicating that these mutations are specific for MSI(+) tumors.

Among the 46 cases with RIZ mutations (19 gastric carcinomas, 6 endometrial carcinomas, 14 colorectal carcinomas, and 7 cell lines), eleven cases (KS15, KS19, E4, E68, E75, E505, AC91, AC334, AC469, HCT-116 and AN3CA) were biallelic mutations. KS15, E68, E505, AC91, AC469 and HCT-116 showed homozygous/hemizygous mutations. KS19 and AC334 had a 1-bp deletion at both the $(A)_8$ and $(A)_9$ tracts in one allele and a 1-bp deletion at the $(A)_9$ tract in the other allele, whereas E4 and AN3CA showed a 1-bp deletion at the $(A)_9$ tract in one allele and a 2-bp deletion at the $(A)_9$ tract in the other allele. E75 had a 1-bp deletion at the $(A)_8$ tract in one allele, and a 2-bp deletion at the $(A)_9$ tract in the other allele.

To determine whether RIZ is also affected by genomic deletions in MSI(+) cancers, loss of heterozygosity (LOH) studies were performed on 25 cases with frameshift mutations for which the matched normal DNAs were available. The RIZ pro704 deletion polymorphism, a three-nucleotide deletion at codon Pro704 in exon 8 (Fang et al., *Genes Chromosomes Cancer* 28:269–275 (2000)), allowed detection of LOH in 2 of 12 informative tumors, KS07 and KS20, which had frameshift mutations in one allele. Therefore, eleven cancers (KS07, KS15, KS19, KS20, E4, E68, E75, E505, AC91, AC334 and AC469) and two cell lines (HCT-116, AN3CA) had evidence of biallelic inactivation of RIZ.

All of the frame shift mutations in RIZ detected in this example are predicted to lead to the production of COOH-terminal domain truncated proteins. The deletion of one adenosine in the $(A)_8$ tract of RIZ produces a stop codon two residues from the tract and a mutant protein lacking the C-terminal 293 amino acids.

It has been demonstrated that the COOH-terminal domain of RIZ1 is a PR domain-binding motif, which may play a role in binding RIZl (RIZ oligomerization) (Huang et al., *J. Biol. Chem.* 273:15933–15940 (1998)). Thus, deletion of this COOH-terminal protein-binding interface is likely to seriously affect RIZl function.

These results show that RIZ frameshift mutations are common in sporadic MSI(+) cancers, including gastric, endometrial and colorectal carcinomas. Many of these mutations are biallelic or homozygous/hemizygous, which suggests that RIZ fits the Knudson two-hit model of tumor suppressor genes (Knudson, *Proc. Natl. Acad. Sci. USA* 68:820–823 (1971)). Given the characteristic low frequency of LOH in MSI(+) tumors, it is not surprising that LOH is not commonly found at the RIZ locus in these tumors.

In view of the recent report of a role of RIZ in estrogen-receptor signaling (Abbondanza et al., *Proc. Natl. Acad. Sci. USA* 97:3130–31135 (2000)), the finding of RIZ mutations in endometrial carcinomas is consistent with an important role in the hormone-dependent growth-control pathways in the endometrium.

EXAMPLE III

RIZ1 Expression Inhibits Growth of MSI(+) Tumors

This examples shows that RIZ1 expression inhibits growth of MSI(+) tumors and induces apoptosis of tumor cells in vivo.

To determine the efficacy of RIZl in gene therapy of MSI(+) tumors, the effect of expression of recombinant RIZl in inhibiting growth of established solid tumors was determined. As a control, the effect of recombinant p53 expression was also assessed.

The MSI(+) HCT116 colorectal cancer cell line (obtained from American Type Culture Collection), which carries homozygously mutated RIZ1 and wild type p53, was cultured in Dulbecco's modified Eagle's medium with 10% fetal calf serum.

Athymic female nu/nu (nude) mice were obtained from Jackson Laboratories (Bar Harbor, Me.). HCT116 tumor cells ($2 \times 10^6$ cells in 100 μl PBS/mouse) were injected subcutaneously into nude mice. Tumors were allowed to grow in vivo for 6 days, at which time they reached an average size of 0.5 cm in diameter. Prior to therapy, the animals were randomized and regrouped by tumor size (5 to 11 mice per group). Mice bearing established HCT116 tumors received intratumoral and peritumoral injection of either PBS alone, or adenovirus suspension ($8 \times 10^{10}$ particles of virus per dose), on every other day for a total of 4 doses.

The adenovirus constructs lacking an insert (Adnull, gift of Prem Seth, National Cancer Institute, Maryland), or expressing either RIZ1 (AdRIZ1) or p53 (Adp53) were prepared, amplified and titered in 293 cells, as described in He et al., *Cancer Res.* 58:4328–4244 (1998).

Tumor sizes were measured 2 to 3 times a week. Tumor volumes were calculated as $a \times b^2 \times 0.5$, where a is the length and b is the width of the tumor in millimeters. Tumor volumes for different treatment groups on each day were compared by Student's t test.

As shown in FIG. 2, in mice treated with either PBS alone, the Adnull virus, or the Adp53 virus, tumors continued to grow aggressively. In contrast, tumors in mice treated with AdRIZ1 virus grew significantly slower.

The effects of RIZ1 and p53 expression on tumor cell apoptosis in established tumors was also determined. HCT116 tumor cells were injected into nude mice, and the xenografts allowed to grow for one month. Virus suspension was injected intratumorally into the established tumors. At day 2 post-injection, tumors were excised, fixed in 10% buffered formalin and embedded in paraffin. Tissue sections were processed for immunohistochemical staining for the expression of RIZ1 or p53, or for the presence of fragmented DNA.

For R1Z1 immunostaining, antiserum 1637 was used at 1:400 dilution. For p53 staining, rabbit serum AB545 (Chemicon, Calif.) was used at 1:200 dilution. Secondary antibodies were peroxidase-labeled goat anti-rabbit IgG. For detection of apoptosis, Apoptag in situ apoptosis detection kits were used (Intergen, Purchase, N.Y.). Samples were assayed as per kit directions. Briefly, deparaffinized, rehydrated tissue sections were treated with proteases, incubated with TdT, and developed using an avidin-peroxidase kit and DAB (DAKO, San Francisco, Calif.). Slides were counterstained with hematoxylin.

Figure 3:
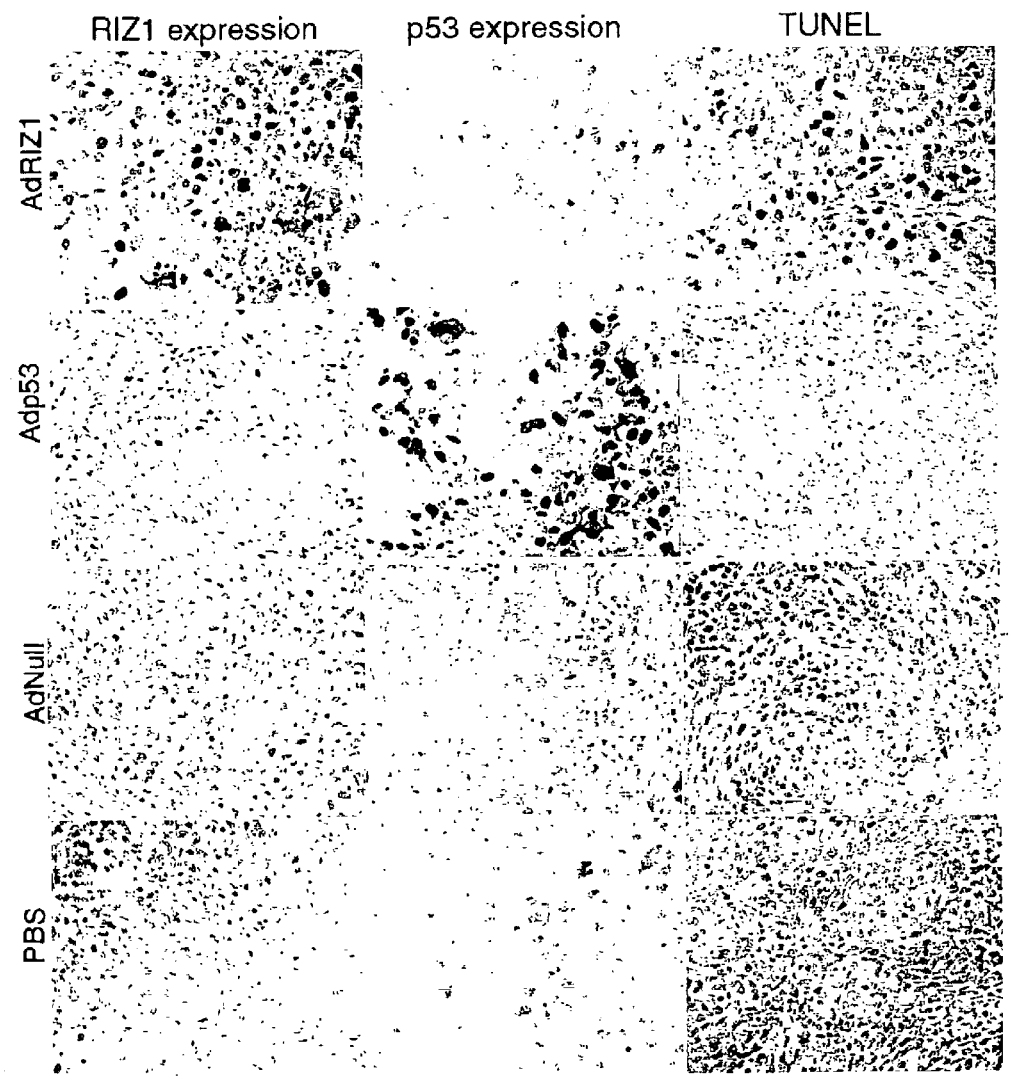
FIG. 3 shows an immunohistochemical analysis of RIZl expression, p53 expression, and apoptosis (TUNEL) in established HCT116 tumors 2 days after injection of either buffer, control Adnull adenovirus, Adp53 adenovirus, or AdRIZl adenovirus.

As shown in FIG. 3, the majority of tumor cells surrounding the injection sites showed strong R1Z1 or p53 nuclear staining in AdRIZ1 or Adp53 virus-injected tumors, respectively. In addition, tumors injected with AdRIZ1, but not Adp53, Adnull, or buffer alone showed strong Apoptag staining, indicating that apoptosis occurred in R1Z1 expressing cells.

In summary, consistent with the in vitro observations described in Example I, above, the preclinical study described above demonstrates that treatment of MSI(+) tumors by introduction of an RIZ1 expression construct inhibits growth and induces apoptosis of the tumor All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of determining MSI status of a tumor selected from a colorectal tumor, a gastric tumor and an endometrial tumor, comprising determining in said tumor the number of adenosine (A) nucleotides in a poly(A) tract located at positions 4393–4400 of SEQ ID NO:3 or 4582–4590 of SEQ ID NO:3 of RIZ nucleic acid molecule in said tumor, wherein an abnormal number of adenosine nucleotides in said RIZ poly(A) tract indicates that the tumor is MSI-positive.

2. The method of claim 1, wherein said poly(A) tract is a RIZ (A)8 tract at positions 4393–4400 of SEQ ID NO:3.

3. The method of claim 1, wherein said poly(A) tract is a RIZ (A)9 tract at positions 4582–4590 of SEQ ID NO:3.

4. The method of claim 1, wherein said abnormal number of adenosine residues is an increased number.

5. The method of claim 1, wherein said abnormal number of adenosine residues is a decreased number.

6. The method of claim 1, wherein a decrease of one or two adenosine nucleotides in said poly(A) tract indicates that the tumor is MSI-positive.

7. The method of claim 6, wherein said tumor is a hereditary nonpolyposis colon carcinoma.

* * * * *

SEQUENCE LISTING

```
<160> NUMBER OF SEQ ID NOS: 15

<210> SEQ ID NO 1
<211> LENGTH: 6171
<212> TYPE: DNA
<213> ORGANISM: Rattus SP.
<220> FEATURE:
<221> NAME/KEY: CDS
<222> LOCATION: (157)...(5274)

<400> SEQUENCE: 1
gccaagatgg cggcggcgcg gccgcgggcg ccagggcgac ggcggcggct gaggctctgg      60
gctcgctgaa gcgttggcac gtcgcgctct gggctcatgt aatcaaagaa gtttctttgt     120
tgtgtgtatc ttcacagaac acaacaggaa ttgaaa atg cat cag aac act gag      174
                                         Met His Gln Asn Thr Glu
                                         1               5 tct gtg gca gcc act gag act ctg gct gag gta cct gaa cat gtg ctt      222
Ser Val Ala Ala Thr Glu Thr Leu Ala Glu Val Pro Glu His Val Leu
         10                  15                  20 cga gga ctt cca gag gaa gta aga ctt ttc cca tct gca gtc gac aag      270
Arg Gly Leu Pro Glu Glu Val Arg Leu Phe Pro Ser Ala Val Asp Lys
     25                  30                  35 act cgg att ggt gtc tgg gct act aaa cca att tta aaa ggg aaa aag      318
```

```
                                                                    -continued Thr Arg Ile Gly Val Trp Ala Thr Lys Pro Ile Leu Lys Gly Lys Lys
    40              45              50 ttt ggg cca ttt gtt ggt gat aag aag aag aga tcc cag gtt agg aat      366
Phe Gly Pro Phe Val Gly Asp Lys Lys Lys Arg Ser Gln Val Arg Asn
55              60              65                              70 aat gtg tac atg tgg gag gtc tac tac cca aat ttg ggg tgg atg tgc      414
Asn Val Tyr Met Trp Glu Val Tyr Tyr Pro Asn Leu Gly Trp Met Cys
                75              80              85 att gat gcc acc gat ccg gag aag ggc aac tgg cta cgc tat gtg aac      462
Ile Asp Ala Thr Asp Pro Glu Lys Gly Asn Trp Leu Arg Tyr Val Asn
            90              95              100 tgg gct tgc tca gga gaa gag cag aat tta ttt cca ctg gaa atc aac      510
Trp Ala Cys Ser Gly Glu Glu Gln Asn Leu Phe Pro Leu Glu Ile Asn
        105             110             115 aga gcc att tac tat aaa acc tta aag cca atc gcg cct ggc gag gag      558
Arg Ala Ile Tyr Tyr Lys Thr Leu Lys Pro Ile Ala Pro Gly Glu Glu
    120             125             130 ctc ctg gtc tgg tac aat ggg gaa gac aac cct gag ata gca gct gcg      606
Leu Leu Val Trp Tyr Asn Gly Glu Asp Asn Pro Glu Ile Ala Ala Ala
135             140             145             150 att gag gaa gag cga gcc agc gcc cgg agc aag cgg agc tcc ccg aag      654
Ile Glu Glu Glu Arg Ala Ser Ala Arg Ser Lys Arg Ser Ser Pro Lys
                155             160             165 agc cgc aga ggg aag aag aaa tca cac gag aac aaa aac aaa ggc atc      702
Ser Arg Arg Gly Lys Lys Lys Ser His Glu Asn Lys Asn Lys Gly Ile
            170             175             180 aga acc cac ccc aca cag ctg aag gca agt gag ctg gac tct acc ttt      750
Arg Thr His Pro Thr Gln Leu Lys Ala Ser Glu Leu Asp Ser Thr Phe
        185             190             195 gca aac atg agg ggc tct gca gaa ggt cca aaa gaa gag gat gag agg      798
Ala Asn Met Arg Gly Ser Ala Glu Gly Pro Lys Glu Glu Asp Glu Arg
    200             205             210 cct ttg gct tcg gca cct gag cag cca gcc cct ctg ccg gag gtg ggg      846
Pro Leu Ala Ser Ala Pro Glu Gln Pro Ala Pro Leu Pro Glu Val Gly
215             220             225             230 aat caa gat gca gtt cca cag gtg gcc atc cct ctc cct gcc tgc gag      894
Asn Gln Asp Ala Val Pro Gln Val Ala Ile Pro Leu Pro Ala Cys Glu
                235             240             245 cca cag cca gag gta gat ggg aaa caa gaa gtc aca gac tgt gag gtc      942
Pro Gln Pro Glu Val Asp Gly Lys Gln Glu Val Thr Asp Cys Glu Val
            250             255             260 aat gat gtg gag gaa gag gag ctg gaa gag gaa gag ctg gaa gag           990
Asn Asp Val Glu Glu Glu Glu Leu Glu Glu Glu Glu Leu Glu Glu
        265             270             275 gag gag gag gag gag ttg gga gaa gat ggg gta gaa gaa gca gac atg     1038
Glu Glu Glu Glu Glu Leu Gly Glu Asp Gly Val Glu Glu Ala Asp Met
    280             285             290 ccg aat gaa agc tct gcg aaa gag ccg gag atc cgg tgt gaa gaa aag     1086
Pro Asn Glu Ser Ser Ala Lys Glu Pro Glu Ile Arg Cys Glu Glu Lys
295             300             305             310 cca gaa gac tta tta gaa gag cca cag agc atg tcg aat gaa gct cgt     1134
Pro Glu Asp Leu Leu Glu Glu Pro Gln Ser Met Ser Asn Glu Ala Arg
                315             320             325 gaa gac tct cca gac gtg acc cct cct ccc cac act ccc aga gct aga     1182
Glu Asp Ser Pro Asp Val Thr Pro Pro Pro His Thr Pro Arg Ala Arg
            330             335             340 gag gag gcc aac ggt gat gta ctt gag aca ttt atg ttt ccg tgt cag     1230
Glu Glu Ala Asn Gly Asp Val Leu Glu Thr Phe Met Phe Pro Cys Gln
        345             350             355
```

-continued

```
cac tgt gaa aga aaa ttt gca acg aag cag ggg cta gag cgt cac atg      1278
His Cys Glu Arg Lys Phe Ala Thr Lys Gln Gly Leu Glu Arg His Met
    360                 365                 370 cac atc cac att tct acc atc aat cat gct ttc aag tgc aag tac tgt      1326
His Ile His Ile Ser Thr Ile Asn His Ala Phe Lys Cys Lys Tyr Cys
375                 380                 385                 390 ggg aaa cgg ttt ggc aca cag att aac agg agg cgt cat gaa cgg cgc      1374
Gly Lys Arg Phe Gly Thr Gln Ile Asn Arg Arg Arg His Glu Arg Arg
                395                 400                 405 cac gaa acg ggg ttg aag aga aga ccc agc atg act tta cag tcc tca      1422
His Glu Thr Gly Leu Lys Arg Arg Pro Ser Met Thr Leu Gln Ser Ser
            410                 415                 420 gag gat cca gat gat ggc aag ggg gaa aat gtt act tct aaa gat gag      1470
Glu Asp Pro Asp Asp Gly Lys Gly Glu Asn Val Thr Ser Lys Asp Glu
        425                 430                 435 tca agt cca cct caa ctc ggg caa gac tgt ttg ata ttg aac tca gag      1518
Ser Ser Pro Pro Gln Leu Gly Gln Asp Cys Leu Ile Leu Asn Ser Glu
    440                 445                 450 aaa acc tca cag gaa gta ctg aat tca tct ttt gtg gaa gaa aat ggt      1566
Lys Thr Ser Gln Glu Val Leu Asn Ser Ser Phe Val Glu Glu Asn Gly
455                 460                 465                 470 gaa gtt aaa gaa ctt cat ccg tgc aaa tac tgc aaa aag gta ttt gga      1614
Glu Val Lys Glu Leu His Pro Cys Lys Tyr Cys Lys Lys Val Phe Gly
                475                 480                 485 act cac acc aat atg aga cga cat cag cgt aga gtt cat gag cgc cac      1662
Thr His Thr Asn Met Arg Arg His Gln Arg Arg Val His Glu Arg His
            490                 495                 500 ctg att ccc aaa ggt gtc agg cga aaa gga gga ctt ctg gaa gag cca      1710
Leu Ile Pro Lys Gly Val Arg Arg Lys Gly Gly Leu Leu Glu Glu Pro
        505                 510                 515 cag cca cca gca gag cag gct cca ccc tcc cag aat gtc tat gtc cca      1758
Gln Pro Pro Ala Glu Gln Ala Pro Pro Ser Gln Asn Val Tyr Val Pro
    520                 525                 530 agc aca gag cca gag gag gaa ggg gaa aca gat gac gtg tac atc atg      1806
Ser Thr Glu Pro Glu Glu Glu Gly Glu Thr Asp Asp Val Tyr Ile Met
535                 540                 545                 550 gac att tct agc aac atc tct gaa aac cta aat tac tat att gac ggt      1854
Asp Ile Ser Ser Asn Ile Ser Glu Asn Leu Asn Tyr Tyr Ile Asp Gly
                555                 560                 565 aag att cag acc aac agc agc act agt aac tgt gat gtg att gag atg      1902
Lys Ile Gln Thr Asn Ser Ser Thr Ser Asn Cys Asp Val Ile Glu Met
            570                 575                 580 gag tct aat tct gca cac ttg tat ggc ata gac tgt ctg ctc act cca      1950
Glu Ser Asn Ser Ala His Leu Tyr Gly Ile Asp Cys Leu Leu Thr Pro
        585                 590                 595 gtg acc gtg gag att act cag aac ata aag agc act cag gtc tct gtg      1998
Val Thr Val Glu Ile Thr Gln Asn Ile Lys Ser Thr Gln Val Ser Val
    600                 605                 610 aca gat gat ctt ctc aaa gac tct ccc agc agc aca aat tgt gag tct      2046
Thr Asp Asp Leu Leu Lys Asp Ser Pro Ser Ser Thr Asn Cys Glu Ser
615                 620                 625                 630 aag aaa cgg agg act gcc agt cca cct gtg ctc ccc aaa att aaa acg      2094
Lys Lys Arg Arg Thr Ala Ser Pro Pro Val Leu Pro Lys Ile Lys Thr
                635                 640                 645 gag acg gag tct gat tcc aca gca ccc tcg tgt tcc tta agt ctg ccc      2142
Glu Thr Glu Ser Asp Ser Thr Ala Pro Ser Cys Ser Leu Ser Leu Pro
            650                 655                 660 ctg agc ata tcc aca gcc gag gtg gtg tcc ttc cat aaa gag aag ggc      2190
Leu Ser Ile Ser Thr Ala Glu Val Val Ser Phe His Lys Glu Lys Gly
        665                 670                 675
```

-continued

| | |
|---|---|
| gtc tat ttg tcg tcc aag ctc aag cag ctt ctt cag acc cag gac aag<br>Val Tyr Leu Ser Ser Lys Leu Lys Gln Leu Leu Gln Thr Gln Asp Lys<br>680                        685                      690 | 2238 |
| ctg acc ctt cct gca ggg ttt tca gca gct gag att cct aag tta ggt<br>Leu Thr Leu Pro Ala Gly Phe Ser Ala Ala Glu Ile Pro Lys Leu Gly<br>695                        700                      705                      710 | 2286 |
| ccc gtg tgc gcg tct gct cct gca tcc atg ttg ccc gtg acc tct agt<br>Pro Val Cys Ala Ser Ala Pro Ala Ser Met Leu Pro Val Thr Ser Ser<br>                715                      720                      725 | 2334 |
| agg ttt aag aga cgc acc agc tct cca ccg agc tct cca cag cac agc<br>Arg Phe Lys Arg Arg Thr Ser Ser Pro Pro Ser Ser Pro Gln His Ser<br>            730                      735                      740 | 2382 |
| cct gcc ctt cga gac ttc ggg aaa cca aat gat ggg aaa gca gca tgg<br>Pro Ala Leu Arg Asp Phe Gly Lys Pro Asn Asp Gly Lys Ala Ala Trp<br>745                        750                      755 | 2430 |
| aca gac aca gtc ctg act tcc aag aaa ccc aag tta gaa agt cgt agt<br>Thr Asp Thr Val Leu Thr Ser Lys Lys Pro Lys Leu Glu Ser Arg Ser<br>760                        765                      770 | 2478 |
| gac tca cca gca tgg agt ttg tct ggg aga gat gaa aga gaa acc gga<br>Asp Ser Pro Ala Trp Ser Leu Ser Gly Arg Asp Glu Arg Glu Thr Gly<br>775                        780                      785                      790 | 2526 |
| agc cct cct tgc ttt gat gaa tac aaa ata tca aag gaa tgg gca gcc<br>Ser Pro Pro Cys Phe Asp Glu Tyr Lys Ile Ser Lys Glu Trp Ala Ala<br>                795                      800                      805 | 2574 |
| agt tct act ttc agc agt gtg tgc aac caa cag cca ttg gat tta tcc<br>Ser Ser Thr Phe Ser Ser Val Cys Asn Gln Gln Pro Leu Asp Leu Ser<br>            810                      815                      820 | 2622 |
| agc ggg gtc aaa cag aag tca gag ggc aca ggc aag act cca gtc cca<br>Ser Gly Val Lys Gln Lys Ser Glu Gly Thr Gly Lys Thr Pro Val Pro<br>825                        830                      835 | 2670 |
| tgg gaa tct gta ttg gat ctc agt gtg cat aaa aag cct tgc gat tct<br>Trp Glu Ser Val Leu Asp Leu Ser Val His Lys Lys Pro Cys Asp Ser<br>840                        845                      850 | 2718 |
| gaa ggc aag gaa ttc aaa gag aac cat ttg gca cag cca gct gca aag<br>Glu Gly Lys Glu Phe Lys Glu Asn His Leu Ala Gln Pro Ala Ala Lys<br>855                        860                      865                      870 | 2766 |
| aag aaa aaa cca acc acc tgt atg ctt caa aag gtt ctc ctc aat gag<br>Lys Lys Lys Pro Thr Thr Cys Met Leu Gln Lys Val Leu Leu Asn Glu<br>                875                      880                      885 | 2814 |
| tat aat ggt gtt agc tta cct aca gaa acc aca cca gag gtg acc agg<br>Tyr Asn Gly Val Ser Leu Pro Thr Glu Thr Thr Pro Glu Val Thr Arg<br>            890                      895                      900 | 2862 |
| agc cca agt cct tgt aaa tcc cca gat aca cag cca gat cct gaa ctt<br>Ser Pro Ser Pro Cys Lys Ser Pro Asp Thr Gln Pro Asp Pro Glu Leu<br>905                        910                      915 | 2910 |
| ggt cct gac tca agt tgc tca gtc ccc act gct gag tct cca cct gaa<br>Gly Pro Asp Ser Ser Cys Ser Val Pro Thr Ala Glu Ser Pro Pro Glu<br>920                        925                      930 | 2958 |
| gtt gtt ggc cct tcc tca ccc cct ctc cag aca gcc tcc tta tcc tcc<br>Val Val Gly Pro Ser Ser Pro Pro Leu Gln Thr Ala Ser Leu Ser Ser<br>935                        940                      945                      950 | 3006 |
| ggt cag ctg cct cct ctc tta acc ccc aca gag cct tct tcc cct ccc<br>Gly Gln Leu Pro Pro Leu Leu Thr Pro Thr Glu Pro Ser Ser Pro Pro<br>                955                      960                      965 | 3054 |
| ccc tgc cct cct gtg tta act gtt gcc act cca cca cct ccc ctc ctt<br>Pro Cys Pro Pro Val Leu Thr Val Ala Thr Pro Pro Pro Pro Leu Leu<br>            970                      975                      980 | 3102 |
| cca acc gtc cct ctc tcc cac ccc tct tct gat gcc tcc cct cag cag<br>Pro Thr Val Pro Leu Ser His Pro Ser Ser Asp Ala Ser Pro Gln Gln | 3150 |

-continued

```
              985                 990                 995
tgt ccc tct ccg ttc tca aac acc act gct cag tct cct ctt ccc att      3198
Cys Pro Ser Pro Phe Ser Asn Thr Thr Ala Gln Ser Pro Leu Pro Ile
    1000                1005                1010 ctc tcc cca aca gtg tct ccc tct ccc tct ccc att cct cct gta gag      3246
Leu Ser Pro Thr Val Ser Pro Ser Pro Ser Pro Ile Pro Pro Val Glu
1015                1020                1025                1030 cca ctt atg tct gct gct tcc cct ggt ccc cca aca ctt tct tcc tcc      3294
Pro Leu Met Ser Ala Ala Ser Pro Gly Pro Pro Thr Leu Ser Ser Ser
                1035                1040                1045 tcc tct tct tcc tct tcc ttc cct tcc tct tcc tgc tcc tcc acc tcc      3342
Ser Ser Ser Ser Ser Ser Phe Pro Ser Ser Cys Ser Ser Thr Ser
    1050                1055                1060 ccc tcc cca ccc cct ctt tca gca gtg tca tct gtg gtt tcc tct ggg      3390
Pro Ser Pro Pro Pro Leu Ser Ala Val Ser Ser Val Val Ser Ser Gly
        1065                1070                1075 gac aac ctg gag gca tct ctg cct gca gta act ttc aaa cag gag gag      3438
Asp Asn Leu Glu Ala Ser Leu Pro Ala Val Thr Phe Lys Gln Glu Glu
    1080                1085                1090 tca gag agt gaa ggt ctg aaa ccc aag gaa gag gcc cca cct gca ggg      3486
Ser Glu Ser Glu Gly Leu Lys Pro Lys Glu Glu Ala Pro Pro Ala Gly
1095                1100                1105                1110 gga cag agt gtg gtc caa gaa aca ttc agc aaa aac ttc att tgc aat      3534
Gly Gln Ser Val Val Gln Glu Thr Phe Ser Lys Asn Phe Ile Cys Asn
                1115                1120                1125 gtc tgt gaa tcg cct ttt ctt tcc att aaa gac cta acc aaa cat tta      3582
Val Cys Glu Ser Pro Phe Leu Ser Ile Lys Asp Leu Thr Lys His Leu
        1130                1135                1140 tcc gtc cat gct gaa gag tgg ccc ttc aaa tgt gag ttt tgt gtg cag      3630
Ser Val His Ala Glu Glu Trp Pro Phe Lys Cys Glu Phe Cys Val Gln
    1145                1150                1155 ctg ttt aag gtt aag act gat cta tca gag cat cga ttt ctg ctt cat      3678
Leu Phe Lys Val Lys Thr Asp Leu Ser Glu His Arg Phe Leu Leu His
    1160                1165                1170 ggg gtt gga aat atc ttt gtg tgt tct gta tgt aag aaa gaa ttt gcc      3726
Gly Val Gly Asn Ile Phe Val Cys Ser Val Cys Lys Lys Glu Phe Ala
1175                1180                1185                1190 ttc tta tgc aat ctg cag cag cac cag cgt gat ctc cac cca gat gag      3774
Phe Leu Cys Asn Leu Gln Gln His Gln Arg Asp Leu His Pro Asp Glu
                1195                1200                1205 gta tgc aca cac cac gag ttt gaa agt ggg acc ctg agg ccc cag aac      3822
Val Cys Thr His His Glu Phe Glu Ser Gly Thr Leu Arg Pro Gln Asn
    1210                1215                1220 ttc aca gac ccc agc aag gcc aat gtt gag cat atg cca agt ttg cca      3870
Phe Thr Asp Pro Ser Lys Ala Asn Val Glu His Met Pro Ser Leu Pro
        1225                1230                1235 gaa gag cct tta gaa act tct aga gag gag gag tta aat gat tcc tct      3918
Glu Glu Pro Leu Glu Thr Ser Arg Glu Glu Glu Leu Asn Asp Ser Ser
    1240                1245                1250 gaa gag ctt tac acg acc atc aaa ata atg gct tct gga ata aag acg      3966
Glu Glu Leu Tyr Thr Thr Ile Lys Ile Met Ala Ser Gly Ile Lys Thr
1255                1260                1265                1270 aag gat cca gat gtt cga ctt ggt ctc aac cag cac tac ccg agc ttt      4014
Lys Asp Pro Asp Val Arg Leu Gly Leu Asn Gln His Tyr Pro Ser Phe
                1275                1280                1285 aaa cct cct cca ttt cag tac cac cat cga aac cct atg ggg ata ggg      4062
Lys Pro Pro Pro Phe Gln Tyr His His Arg Asn Pro Met Gly Ile Gly
                1290                1295                1300 gtg aca gcc acc aac ttc acc acc cac aat att cca cag act ttc act      4110
Val Thr Ala Thr Asn Phe Thr Thr His Asn Ile Pro Gln Thr Phe Thr
```

```
                Val Thr Ala Thr Asn Phe Thr Thr His Asn Ile Pro Gln Thr Phe Thr
                                1305                1310                1315 act gcc atc cgc tgc aca aag tgt ggg aag ggc gtc gac aat atg cct          4158
Thr Ala Ile Arg Cys Thr Lys Cys Gly Lys Gly Val Asp Asn Met Pro
    1320                1325                1330 gag ctg cat aag cat atc ttg gcg tgt gcg tct gca agt gac aag aag          4206
Glu Leu His Lys His Ile Leu Ala Cys Ala Ser Ala Ser Asp Lys Lys
1335                1340                1345                1350 agg tac acc cct aag aaa aac cca gtg ccc ctg aaa caa act gtg cag          4254
Arg Tyr Thr Pro Lys Lys Asn Pro Val Pro Leu Lys Gln Thr Val Gln
                1355                1360                1365 ccc aaa aat gga gtg gtg gtt cta gac aac tct ggg aaa aat gcc ttc          4302
Pro Lys Asn Gly Val Val Val Leu Asp Asn Ser Gly Lys Asn Ala Phe
        1370                1375                1380 aga cgg atg ggg cag ccc aag aga ctg agc ttc aat gtt gaa ctg ggt          4350
Arg Arg Met Gly Gln Pro Lys Arg Leu Ser Phe Asn Val Glu Leu Gly
            1385                1390                1395 aaa atg tct cca aac aag ctc aag ctg agt gcg ctg aag aag aaa aac          4398
Lys Met Ser Pro Asn Lys Leu Lys Leu Ser Ala Leu Lys Lys Lys Asn
    1400                1405                1410 cag ctg gtg cag aag gcc atc ctt cag aag aac aga gcc gcg aag cag          4446
Gln Leu Val Gln Lys Ala Ile Leu Gln Lys Asn Arg Ala Ala Lys Gln
1415                1420                1425                1430 aag gcg gac ctg agg gat act tcc gag gcg tcc tca cac atc tgc ccg          4494
Lys Ala Asp Leu Arg Asp Thr Ser Glu Ala Ser Ser His Ile Cys Pro
                1435                1440                1445 tac tgt gac agg gag ttc aca tac att ggc agc ctg aat aag cat gcc          4542
Tyr Cys Asp Arg Glu Phe Thr Tyr Ile Gly Ser Leu Asn Lys His Ala
        1450                1455                1460 gcc ttc agc tgt cct aaa aaa cct ctt tct cct tcc aaa aga aaa gtt          4590
Ala Phe Ser Cys Pro Lys Lys Pro Leu Ser Pro Ser Lys Arg Lys Val
            1465                1470                1475 tcc cat tcg tct aag aaa ggt ggc cat gca tca tct tct agc agt gac          4638
Ser His Ser Ser Lys Lys Gly Gly His Ala Ser Ser Ser Ser Ser Asp
    1480                1485                1490 aga aac agc agc tgc cac ccc cgg agg cgg act gca gat acc gag atc          4686
Arg Asn Ser Ser Cys His Pro Arg Arg Arg Thr Ala Asp Thr Glu Ile
1495                1500                1505                1510 aag atg cag agc acg cag gca ccc ttg ggc aag acc aga gct cgg agt          4734
Lys Met Gln Ser Thr Gln Ala Pro Leu Gly Lys Thr Arg Ala Arg Ser
                1515                1520                1525 aca ggc ccc gcc cag gcc tca ctg ccc tcc tcg tcc ttc aga tcc aga          4782
Thr Gly Pro Ala Gln Ala Ser Leu Pro Ser Ser Ser Phe Arg Ser Arg
        1530                1535                1540 cag aat gtc aaa ttt gca gct tca gtg aaa tcc aaa aaa gca agc tct          4830
Gln Asn Val Lys Phe Ala Ala Ser Val Lys Ser Lys Lys Ala Ser Ser
            1545                1550                1555 tca tcc ttg agg aat tcc agt ccc ata aga atg gcc aaa att act cac          4878
Ser Ser Leu Arg Asn Ser Ser Pro Ile Arg Met Ala Lys Ile Thr His
    1560                1565                1570 gtc gag ggc aaa aaa ccc aaa gct gtt gcc aag agt cat tct gct cag          4926
Val Glu Gly Lys Lys Pro Lys Ala Val Ala Lys Ser His Ser Ala Gln
1575                1580                1585                1590 ctc tca agc aaa tcc tcc cga ggc ctg cat gtc aga gtg cag aag agc          4974
Leu Ser Ser Lys Ser Ser Arg Gly Leu His Val Arg Val Gln Lys Ser
                1595                1600                1605 aaa gct gtc ata cag agc aag act gcc ctg gcc agt aag agg aga aca          5022
Lys Ala Val Ile Gln Ser Lys Thr Ala Leu Ala Ser Lys Arg Arg Thr
        1610                1615                1620
```

-continued

| | | | | | | | | | | | | | | |
|---|---|---|---|---|---|---|---|---|---|---|---|---|---|---|
| gac | cgg | ttc | ata | gtg | aaa | tct | aga | gag | cgc | agc | ggg | ggc | cca | atc | acc | 5070 |
| Asp | Arg | Phe | Ile | Val | Lys | Ser | Arg | Glu | Arg | Ser | Gly | Gly | Pro | Ile | Thr |
| | | 1625 | | | | 1630 | | | | 1635 | | | | |

```
gac cgg ttc ata gtg aaa tct aga gag cgc agc ggg ggc cca atc acc    5070
Asp Arg Phe Ile Val Lys Ser Arg Glu Arg Ser Gly Gly Pro Ile Thr
        1625                1630                1635 cga agc ctt cag ctg gca gct gct gcg gac ctg agt gaa agc agg aga    5118
Arg Ser Leu Gln Leu Ala Ala Ala Ala Asp Leu Ser Glu Ser Arg Arg
    1640                1645                1650 gag gac agc agt gcc agg cat gag ctg aag gac ttc agc tac agt ctc    5166
Glu Asp Ser Ser Ala Arg His Glu Leu Lys Asp Phe Ser Tyr Ser Leu
1655                1660                1665                1670 cgc ctg gca tct cga tgc ggc tca tca aca gcc tct tac atc acc aga    5214
Arg Leu Ala Ser Arg Cys Gly Ser Ser Thr Ala Ser Tyr Ile Thr Arg
            1675                1680                1685 caa tgc aga aag gtc aag gcc gcc gca gca act ccg ttc cag gga ccc    5262
Gln Cys Arg Lys Val Lys Ala Ala Ala Ala Thr Pro Phe Gln Gly Pro
        1690                1695                1700 ttc ctc aaa gag taggcactct gtctgctcct taacagcacc tgaagtgacc        5314
Phe Leu Lys Glu
        1705 tggaatcagt gaagccaaag ggaccagcag tctgccctgc agagagcact gacctctccc  5374 agttgtgaga gtgagagaac gagagagaga gagagagaga gagagagaga gagagagaga  5434 gagaatgaga atgtgtgtgt gtgtgtgctg gtgcatgtgt gtggtcttca agccaaggtc  5494 ccagcctcag gagcaggacc ttcccatttc ccgtcatcct ctggatgatc cttgacgtgg  5554 gcccagaacc gtgctctgtg gtgcagccat cctgcccggg aggggcatct ccttctatgc  5614 aattttttta aagagttcct tggccctgct ttgtgcttct tgagctgtcc gtttgccacc  5674 actgggactt ggatctggcc ctgaggggtg gggaagaggg cctatctaag gataacttt   5734 cagaggtcaa gctcccttc atgccacccc tccccctgc cctcaccgac cttttcccca    5794 cactgtctct gggaatcaat agcagatagc atatagatcc atcaggttg agcctgaacc   5854 tcggccctag cactaggaaa tccccttttt ctccctaagc aactggagcc gccagctttc  5914 aagtcatttc ctcctttgag gttctagagt ccgagagtct gctccgaagt ctctcctggg  5974 aacccgggag ccctcgcacc caggacgcag actctgtgcc cattcttaga cctgaggtag  6034 aagaagcagt gttttgggac gataggggtgg aggcgtgcct actttgtctc ctctggtggg 6094 acctcctaca tcattggcat ctgaaccttg caagttcgct gcaaagagaa gcaaaggaaa  6154 aaaaaaaaaa aaaaaaa                                                6171
```

<210> SEQ ID NO 2
<211> LENGTH: 1706
<212> TYPE: PRT
<213> ORGANISM: Rattus SP.

<400> SEQUENCE: 2

```
Met His Gln Asn Thr Glu Ser Val Ala Thr Glu Thr Leu Ala Glu
1               5                   10                  15

Val Pro Glu His Val Leu Arg Gly Leu Pro Glu Val Arg Leu Phe
                20                  25                  30

Pro Ser Ala Val Asp Lys Thr Arg Ile Gly Val Trp Ala Thr Lys Pro
        35                  40                  45

Ile Leu Lys Gly Lys Lys Phe Gly Pro Phe Val Gly Asp Lys Lys
    50                  55                  60

Arg Ser Gln Val Arg Asn Asn Val Tyr Met Trp Glu Val Tyr Tyr Pro
65                  70                  75                  80

Asn Leu Gly Trp Met Cys Ile Asp Ala Thr Asp Pro Glu Lys Gly Asn
                85                  90                  95
```

-continued

```
Trp Leu Arg Tyr Val Asn Trp Ala Cys Ser Gly Glu Glu Gln Asn Leu
                100                 105                 110

Phe Pro Leu Glu Ile Asn Arg Ala Ile Tyr Tyr Lys Thr Leu Lys Pro
            115                 120                 125

Ile Ala Pro Gly Glu Glu Leu Leu Val Trp Tyr Asn Gly Glu Asp Asn
        130                 135                 140

Pro Glu Ile Ala Ala Ile Glu Glu Arg Ala Ser Ala Arg Ser
145                 150                 155                 160

Lys Arg Ser Ser Pro Lys Ser Arg Arg Gly Lys Lys Ser His Glu
                165                 170                 175

Asn Lys Asn Lys Gly Ile Arg Thr His Pro Thr Gln Leu Lys Ala Ser
            180                 185                 190

Glu Leu Asp Ser Thr Phe Ala Asn Met Arg Gly Ser Ala Glu Gly Pro
        195                 200                 205

Lys Glu Glu Asp Glu Arg Pro Leu Ala Ser Ala Pro Glu Gln Pro Ala
    210                 215                 220

Pro Leu Pro Glu Val Gly Asn Gln Asp Ala Val Pro Gln Val Ala Ile
225                 230                 235                 240

Pro Leu Pro Ala Cys Glu Pro Gln Pro Glu Val Asp Gly Lys Gln Glu
                245                 250                 255

Val Thr Asp Cys Glu Val Asn Asp Val Glu Glu Glu Leu Glu Glu
            260                 265                 270

Glu Glu Glu Leu Glu Glu Glu Glu Glu Leu Gly Glu Asp Gly
        275                 280                 285

Val Glu Glu Ala Asp Met Pro Asn Glu Ser Ser Ala Lys Glu Pro Glu
    290                 295                 300

Ile Arg Cys Glu Glu Lys Pro Glu Asp Leu Leu Glu Glu Pro Gln Ser
305                 310                 315                 320

Met Ser Asn Glu Ala Arg Glu Asp Ser Pro Asp Val Thr Pro Pro
                325                 330                 335

His Thr Pro Arg Ala Arg Glu Glu Ala Asn Gly Asp Val Leu Glu Thr
            340                 345                 350

Phe Met Phe Pro Cys Gln His Cys Glu Arg Lys Phe Ala Thr Lys Gln
        355                 360                 365

Gly Leu Glu Arg His Met His Ile His Ile Ser Thr Ile Asn His Ala
    370                 375                 380

Phe Lys Cys Lys Tyr Cys Gly Lys Arg Phe Gly Thr Gln Ile Asn Arg
385                 390                 395                 400

Arg Arg His Glu Arg Arg His Glu Thr Gly Leu Lys Arg Pro Ser
                405                 410                 415

Met Thr Leu Gln Ser Ser Glu Asp Pro Asp Asp Gly Lys Gly Glu Asn
            420                 425                 430

Val Thr Ser Lys Asp Glu Ser Ser Pro Pro Gln Leu Gly Gln Asp Cys
        435                 440                 445

Leu Ile Leu Asn Ser Glu Lys Thr Ser Gln Glu Val Leu Asn Ser Ser
    450                 455                 460

Phe Val Glu Glu Asn Gly Glu Val Lys Glu Leu His Pro Cys Lys Tyr
465                 470                 475                 480

Cys Lys Lys Val Phe Gly Thr His Thr Asn Met Arg Arg His Gln Arg
                485                 490                 495

Arg Val His Glu Arg His Leu Ile Pro Lys Gly Val Arg Arg Lys Gly
            500                 505                 510
```

-continued

```
Gly Leu Leu Glu Glu Pro Gln Pro Ala Glu Gln Ala Pro Pro Ser
            515                 520                 525

Gln Asn Val Tyr Val Pro Ser Thr Glu Pro Glu Glu Gly Glu Thr
            530                 535                 540

Asp Asp Val Tyr Ile Met Asp Ile Ser Ser Asn Ile Ser Glu Asn Leu
545                 550                 555                 560

Asn Tyr Tyr Ile Asp Gly Lys Ile Gln Thr Asn Ser Ser Thr Ser Asn
                565                 570                 575

Cys Asp Val Ile Glu Met Glu Ser Asn Ser Ala His Leu Tyr Gly Ile
                580                 585                 590

Asp Cys Leu Leu Thr Pro Val Thr Val Glu Ile Thr Gln Asn Ile Lys
            595                 600                 605

Ser Thr Gln Val Ser Val Thr Asp Asp Leu Leu Lys Asp Ser Pro Ser
            610                 615                 620

Ser Thr Asn Cys Glu Ser Lys Lys Arg Arg Thr Ala Ser Pro Pro Val
625                 630                 635                 640

Leu Pro Lys Ile Lys Thr Glu Thr Glu Ser Asp Ser Thr Ala Pro Ser
                645                 650                 655

Cys Ser Leu Ser Leu Pro Leu Ser Ile Ser Thr Ala Glu Val Val Ser
            660                 665                 670

Phe His Lys Glu Lys Gly Val Tyr Leu Ser Ser Lys Leu Lys Gln Leu
            675                 680                 685

Leu Gln Thr Gln Asp Lys Leu Thr Leu Pro Ala Gly Phe Ser Ala Ala
            690                 695                 700

Glu Ile Pro Lys Leu Gly Pro Val Cys Ala Ser Ala Pro Ala Ser Met
705                 710                 715                 720

Leu Pro Val Thr Ser Ser Arg Phe Lys Arg Arg Thr Ser Ser Pro Pro
                725                 730                 735

Ser Ser Pro Gln His Ser Pro Ala Leu Arg Asp Phe Gly Lys Pro Asn
            740                 745                 750

Asp Gly Lys Ala Ala Trp Thr Asp Thr Val Leu Thr Ser Lys Lys Pro
            755                 760                 765

Lys Leu Glu Ser Arg Ser Asp Ser Pro Ala Trp Ser Leu Ser Gly Arg
            770                 775                 780

Asp Glu Arg Glu Thr Gly Ser Pro Pro Cys Phe Asp Glu Tyr Lys Ile
785                 790                 795                 800

Ser Lys Glu Trp Ala Ala Ser Ser Thr Phe Ser Ser Val Cys Asn Gln
                805                 810                 815

Gln Pro Leu Asp Leu Ser Ser Gly Val Lys Gln Lys Ser Glu Gly Thr
            820                 825                 830

Gly Lys Thr Pro Val Pro Trp Glu Ser Val Leu Asp Leu Ser Val His
            835                 840                 845

Lys Lys Pro Cys Asp Ser Glu Gly Lys Glu Phe Lys Glu Asn His Leu
850                 855                 860

Ala Gln Pro Ala Ala Lys Lys Lys Pro Thr Thr Cys Met Leu Gln
865                 870                 875                 880

Lys Val Leu Leu Asn Glu Tyr Asn Gly Val Ser Leu Pro Thr Glu Thr
                885                 890                 895

Thr Pro Glu Val Thr Arg Ser Pro Ser Pro Cys Lys Ser Pro Asp Thr
            900                 905                 910

Gln Pro Asp Pro Glu Leu Gly Pro Asp Ser Ser Cys Ser Val Pro Thr
            915                 920                 925

Ala Glu Ser Pro Pro Glu Val Val Gly Pro Ser Ser Pro Pro Leu Gln
```

-continued

```
            930                 935                 940
Thr Ala Ser Leu Ser Ser Gly Gln Leu Pro Pro Leu Leu Thr Pro Thr
945                 950                 955                 960
Glu Pro Ser Ser Pro Pro Cys Pro Pro Val Leu Thr Val Ala Thr
                965                 970                 975
Pro Pro Pro Pro Leu Leu Pro Thr Val Pro Leu Ser His Pro Ser Ser
                980                 985                 990
Asp Ala Ser Pro Gln Gln Cys Pro Ser Pro Phe Ser Asn Thr Thr Ala
            995                 1000                1005
Gln Ser Pro Leu Pro Ile Leu Ser Pro Thr Val Ser Pro Ser Pro Ser
        1010                1015                1020
Pro Ile Pro Pro Val Glu Pro Leu Met Ser Ala Ala Ser Pro Gly Pro
1025                1030                1035                1040
Pro Thr Leu Ser Ser Ser Ser Ser Ser Ser Ser Phe Pro Ser Ser
                1045                1050                1055
Ser Cys Ser Ser Thr Ser Pro Ser Pro Pro Leu Ser Ala Val Ser
                1060                1065                1070
Ser Val Val Ser Ser Gly Asp Asn Leu Glu Ala Ser Leu Pro Ala Val
        1075                1080                1085
Thr Phe Lys Gln Glu Glu Ser Glu Ser Glu Gly Leu Lys Pro Lys Glu
        1090                1095                1100
Glu Ala Pro Pro Ala Gly Gly Gln Ser Val Val Gln Glu Thr Phe Ser
1105                1110                1115                1120
Lys Asn Phe Ile Cys Asn Val Cys Glu Ser Pro Phe Leu Ser Ile Lys
                1125                1130                1135
Asp Leu Thr Lys His Leu Ser Val His Ala Glu Glu Trp Pro Phe Lys
                1140                1145                1150
Cys Glu Phe Cys Val Gln Leu Phe Lys Val Lys Thr Asp Leu Ser Glu
                1155                1160                1165
His Arg Phe Leu Leu His Gly Val Gly Asn Ile Phe Val Cys Ser Val
                1170                1175                1180
Cys Lys Lys Glu Phe Ala Phe Leu Cys Asn Leu Gln Gln His Gln Arg
1185                1190                1195                1200
Asp Leu His Pro Asp Glu Val Cys Thr His His Glu Phe Glu Ser Gly
                1205                1210                1215
Thr Leu Arg Pro Gln Asn Phe Thr Asp Pro Ser Lys Ala Asn Val Glu
            1220                1225                1230
His Met Pro Ser Leu Pro Glu Glu Pro Leu Glu Thr Ser Arg Glu Glu
            1235                1240                1245
Glu Leu Asn Asp Ser Ser Glu Glu Leu Tyr Thr Thr Ile Lys Ile Met
        1250                1255                1260
Ala Ser Gly Ile Lys Thr Lys Asp Pro Asp Val Arg Leu Gly Leu Asn
1265                1270                1275                1280
Gln His Tyr Pro Ser Phe Lys Pro Pro Phe Gln Tyr His His Arg
            1285                1290                1295
Asn Pro Met Gly Ile Gly Val Thr Ala Thr Asn Phe Thr Thr His Asn
            1300                1305                1310
Ile Pro Gln Thr Phe Thr Thr Ala Ile Arg Cys Thr Lys Cys Gly Lys
            1315                1320                1325
Gly Val Asp Asn Met Pro Glu Leu His Lys His Ile Leu Ala Cys Ala
        1330                1335                1340
Ser Ala Ser Asp Lys Lys Arg Tyr Thr Pro Lys Lys Asn Pro Val Pro
1345                1350                1355                1360
```

```
Leu Lys Gln Thr Val Gln Pro Lys Asn Gly Val Val Leu Asp Asn
            1365                1370                1375

Ser Gly Lys Asn Ala Phe Arg Arg Met Gly Gln Pro Lys Arg Leu Ser
        1380                1385                1390

Phe Asn Val Glu Leu Gly Lys Met Ser Pro Asn Lys Leu Lys Leu Ser
    1395                1400                1405

Ala Leu Lys Lys Lys Asn Gln Leu Val Gln Lys Ala Ile Leu Gln Lys
1410                1415                1420

Asn Arg Ala Ala Lys Gln Lys Ala Asp Leu Arg Asp Thr Ser Glu Ala
1425                1430                1435                1440

Ser Ser His Ile Cys Pro Tyr Cys Asp Arg Glu Phe Thr Tyr Ile Gly
            1445                1450                1455

Ser Leu Asn Lys His Ala Ala Phe Ser Cys Pro Lys Lys Pro Leu Ser
        1460                1465                1470

Pro Ser Lys Arg Lys Val Ser His Ser Lys Lys Gly Gly His Ala
    1475                1480                1485

Ser Ser Ser Ser Ser Asp Arg Asn Ser Ser Cys His Pro Arg Arg Arg
1490                1495                1500

Thr Ala Asp Thr Glu Ile Lys Met Gln Ser Thr Gln Ala Pro Leu Gly
1505                1510                1515                1520

Lys Thr Arg Ala Arg Ser Thr Gly Pro Ala Gln Ala Ser Leu Pro Ser
            1525                1530                1535

Ser Ser Phe Arg Ser Arg Gln Asn Val Lys Phe Ala Ala Ser Val Lys
        1540                1545                1550

Ser Lys Lys Ala Ser Ser Ser Ser Leu Arg Asn Ser Ser Pro Ile Arg
    1555                1560                1565

Met Ala Lys Ile Thr His Val Glu Gly Lys Lys Pro Lys Ala Val Ala
    1570                1575                1580

Lys Ser His Ser Ala Gln Leu Ser Ser Lys Ser Ser Arg Gly Leu His
1585                1590                1595                1600

Val Arg Val Gln Lys Ser Lys Ala Val Ile Gln Ser Lys Thr Ala Leu
            1605                1610                1615

Ala Ser Lys Arg Arg Thr Asp Arg Phe Ile Val Lys Ser Arg Glu Arg
        1620                1625                1630

Ser Gly Gly Pro Ile Thr Arg Ser Leu Gln Leu Ala Ala Ala Ala Asp
    1635                1640                1645

Leu Ser Glu Ser Arg Arg Glu Asp Ser Ser Ala Arg His Glu Leu Lys
    1650                1655                1660

Asp Phe Ser Tyr Ser Leu Arg Leu Ala Ser Arg Cys Gly Ser Ser Thr
1665                1670                1675                1680

Ala Ser Tyr Ile Thr Arg Gln Cys Arg Lys Val Lys Ala Ala Ala Ala
            1685                1690                1695

Thr Pro Phe Gln Gly Pro Phe Leu Lys Glu
        1700                1705

<210> SEQ ID NO 3
<211> LENGTH: 5868
<212> TYPE: DNA
<213> ORGANISM: Homo sapien
<220> FEATURE:
<221> NAME/KEY: CDS
<222> LOCATION: (121)...(5277)

<400> SEQUENCE: 3
ggaaaattta ttcccactgg aaatcaacag agccatttac tataaaactt taaagggttc     60
```

-continued

```
atgtaatcaa agaagtttct tgtgtgtgtg tatctttaca gaacacaaca ggaattgaaa      120 atg aat cag aac act act gag cct gtg gcg gcc acc gag acc ctg gct       168
Met Asn Gln Asn Thr Thr Glu Pro Val Ala Ala Thr Glu Thr Leu Ala
1               5                   10                  15 gag gta ccc gaa cat gtg ctg cga gga ctt ccg gag gaa gtg agg ctt       216
Glu Val Pro Glu His Val Leu Arg Gly Leu Pro Glu Glu Val Arg Leu
            20                  25                  30 ttc cct tct gct gtt gac aag acc cgg att ggt gtc tgg gcc act aaa       264
Phe Pro Ser Ala Val Asp Lys Thr Arg Ile Gly Val Trp Ala Thr Lys
        35                  40                  45 cca att tta aaa ggg aaa aaa ttt ggg cca ttt gtt ggt gat aag aaa       312
Pro Ile Leu Lys Gly Lys Lys Phe Gly Pro Phe Val Gly Asp Lys Lys
    50                  55                  60 aaa aga tct cag gtt aag aat aat gta tac atg tgg gag gtg tat tac       360
Lys Arg Ser Gln Val Lys Asn Asn Val Tyr Met Trp Glu Val Tyr Tyr
65                  70                  75                  80 cca aat ttg gga tgg atg tgc att gat gcc act gat cca gag aag gga       408
Pro Asn Leu Gly Trp Met Cys Ile Asp Ala Thr Asp Pro Glu Lys Gly
                85                  90                  95 aac tgg ctg cga tat gtg aat tgg gct tgc tca gga gaa gag caa aat       456
Asn Trp Leu Arg Tyr Val Asn Trp Ala Cys Ser Gly Glu Glu Gln Asn
            100                 105                 110 tta ttc cca ctg gaa atc aac aga gcc att tac tat aaa act tta aag       504
Leu Phe Pro Leu Glu Ile Asn Arg Ala Ile Tyr Tyr Lys Thr Leu Lys
        115                 120                 125 cca atc gcg ccg ggc gag gag ctc ctg gtc tgg tac aat ggg gaa gac       552
Pro Ile Ala Pro Gly Glu Glu Leu Leu Val Trp Tyr Asn Gly Glu Asp
    130                 135                 140 aac cct gag ata gca gct gcg att gag gaa gag cga gcc agc gcc cgg       600
Asn Pro Glu Ile Ala Ala Ala Ile Glu Glu Glu Arg Ala Ser Ala Arg
145                 150                 155                 160 agc aag cgg agc tcc ccc aag agc cgg aaa ggg aag aaa aaa tcc cag       648
Ser Lys Arg Ser Ser Pro Lys Ser Arg Lys Gly Lys Lys Lys Ser Gln
                165                 170                 175 gaa aat aaa aac aaa gga aac aaa atc caa gac ata caa ctg aag aca       696
Glu Asn Lys Asn Lys Gly Asn Lys Ile Gln Asp Ile Gln Leu Lys Thr
            180                 185                 190 agt gag cca gat ttc acc tct gca aat atg aga gat tct gca gaa ggt       744
Ser Glu Pro Asp Phe Thr Ser Ala Asn Met Arg Asp Ser Ala Glu Gly
        195                 200                 205 cct aaa gaa gac gaa gag aag cct tca gcc tca gca ctt gag cag ccg       792
Pro Lys Glu Asp Glu Glu Lys Pro Ser Ala Ser Ala Leu Glu Gln Pro
    210                 215                 220 gcc acc ctc cag gag gtg gcc agt cag gag gtg cct cca gaa cta gca       840
Ala Thr Leu Gln Glu Val Ala Ser Gln Glu Val Pro Pro Glu Leu Ala
225                 230                 235                 240 acc cct gcc cct gcc tgg gag cca cag cca gaa cca gac gag cga tta       888
Thr Pro Ala Pro Ala Trp Glu Pro Gln Pro Glu Pro Asp Glu Arg Leu
                245                 250                 255 gaa gcg gca gct tgt gag gtg aat gat ttg ggg gaa gag gag gag gag       936
Glu Ala Ala Ala Cys Glu Val Asn Asp Leu Gly Glu Glu Glu Glu Glu
            260                 265                 270 gaa gag gag gag gat gaa gaa gaa gaa gat gat gat gat gat gag           984
Glu Glu Glu Glu Asp Glu Glu Glu Glu Asp Asp Asp Asp Asp Glu
        275                 280                 285 ttg gaa gac gag ggg gaa gaa gaa gcc agc atg cca aat gaa aat tct      1032
Leu Glu Asp Glu Gly Glu Glu Glu Ala Ser Met Pro Asn Glu Asn Ser
    290                 295                 300
```

-continued

| | | |
|---|---|---|
| gtg aaa gag cca gaa ata cgg tgt gat gag aag cca gaa gat tta tta<br>Val Lys Glu Pro Glu Ile Arg Cys Asp Glu Lys Pro Glu Asp Leu Leu<br>305                      310                     315                   320 | 1080 |
| gag gaa cca aaa aca act tca gaa gaa act ctt gaa gac tgc tca gag<br>Glu Glu Pro Lys Thr Thr Ser Glu Glu Thr Leu Glu Asp Cys Ser Glu<br>                   325                   330                   335 | 1128 |
| gta aca cct gcc atg caa atc ccc aga act aaa gaa gag gcc aat ggt<br>Val Thr Pro Ala Met Gln Ile Pro Arg Thr Lys Glu Glu Ala Asn Gly<br>           340                   345                   350 | 1176 |
| gat gta ttt gaa acg ttt atg ttt ccg tgt caa cat tgt gaa agg aag<br>Asp Val Phe Glu Thr Phe Met Phe Pro Cys Gln His Cys Glu Arg Lys<br>355                     360                   365 | 1224 |
| ttt aca acc aaa cag ggg ctt gag cgt cac atg cat atc cat ata tcc<br>Phe Thr Thr Lys Gln Gly Leu Glu Arg His Met His Ile His Ile Ser<br>370                     375                   380 | 1272 |
| acc gtc aat cat gct ttc aaa tgc aag tac tgt ggg aaa gcc ttt ggc<br>Thr Val Asn His Ala Phe Lys Cys Lys Tyr Cys Gly Lys Ala Phe Gly<br>385                     390                   395                   400 | 1320 |
| aca cag att aac cgg cgg cga cat gag cgg cgc cat gaa gca ggg tta<br>Thr Gln Ile Asn Arg Arg Arg His Glu Arg Arg His Glu Ala Gly Leu<br>                               405                   410                   415 | 1368 |
| aag cgg aaa ccc agc caa aca cta cag ccg tca gag gat ctg gct gat<br>Lys Arg Lys Pro Ser Gln Thr Leu Gln Pro Ser Glu Asp Leu Ala Asp<br>           420                   425                   430 | 1416 |
| ggc aaa gca tct gga gaa aac gtt gct tca aaa gat gat tcg agt cct<br>Gly Lys Ala Ser Gly Glu Asn Val Ala Ser Lys Asp Asp Ser Ser Pro<br>435                     440                   445 | 1464 |
| ccc agt ctt ggg cca gac tgt ctg atc atg aat tca gag aag gct tcc<br>Pro Ser Leu Gly Pro Asp Cys Leu Ile Met Asn Ser Glu Lys Ala Ser<br>           450                   455                   460 | 1512 |
| caa gac aca ata aat tct tct gtc gta gaa gag aat ggg gaa gtt aaa<br>Gln Asp Thr Ile Asn Ser Ser Val Val Glu Glu Asn Gly Glu Val Lys<br>465                     470                   475                   480 | 1560 |
| gaa ctt cat ccg tgc aaa tat tgt aaa aag gtt ttt gga act cat act<br>Glu Leu His Pro Cys Lys Tyr Cys Lys Lys Val Phe Gly Thr His Thr<br>                   485                   490                   495 | 1608 |
| aat atg aga cgg cat cag cgt aga gtt cac gaa cgt cat ctg att ccc<br>Asn Met Arg Arg His Gln Arg Arg Val His Glu Arg His Leu Ile Pro<br>           500                   505                   510 | 1656 |
| aaa ggt gta cgg cga aaa gga ggc ctt gaa gag ccc cag cct cca gca<br>Lys Gly Val Arg Arg Lys Gly Gly Leu Glu Glu Pro Gln Pro Pro Ala<br>515                     520                   525 | 1704 |
| gaa cag gcc cag gcc acc cag aac gtg tat gta cca agc aca gag ccg<br>Glu Gln Ala Gln Ala Thr Gln Asn Val Tyr Val Pro Ser Thr Glu Pro<br>530                     535                   540 | 1752 |
| gag gag gaa ggg gaa gca gat gat gtg tac atc atg gac att tct agc<br>Glu Glu Glu Gly Glu Ala Asp Asp Val Tyr Ile Met Asp Ile Ser Ser<br>545                     550                   555                   560 | 1800 |
| aat atc tct gaa aac tta aat tac tat att gat ggt aaa att caa act<br>Asn Ile Ser Glu Asn Leu Asn Tyr Tyr Ile Asp Gly Lys Ile Gln Thr<br>                   565                   570                   575 | 1848 |
| aat aac aac act agt aac tgt gat gtg att gag atg gag tct gct tcg<br>Asn Asn Asn Thr Ser Asn Cys Asp Val Ile Glu Met Glu Ser Ala Ser<br>           580                   585                   590 | 1896 |
| gca gat ttg tat ggt ata aat tgt ctg ctc act cca gtt aca gtg gaa<br>Ala Asp Leu Tyr Gly Ile Asn Cys Leu Leu Thr Pro Val Thr Val Glu<br>595                     600                   605 | 1944 |
| att act caa aat ata aag acc aca cag gtc cct gta aca gaa gat ctt<br>Ile Thr Gln Asn Ile Lys Thr Thr Gln Val Pro Val Thr Glu Asp Leu<br>           610                   615                   620 | 1992 |

```
cct aaa gag cct ttg ggc agc aca aat agt gag gcc aag aag cgg aga         2040
Pro Lys Glu Pro Leu Gly Ser Thr Asn Ser Glu Ala Lys Lys Arg Arg
625                 630                 635                 640 act gcg agc cca cct gca ctg ccc aaa att aag gcc gaa aca gac tct         2088
Thr Ala Ser Pro Pro Ala Leu Pro Lys Ile Lys Ala Glu Thr Asp Ser
        645                 650                 655 gac ccc atg gtc ccc tct tgc tct tta agt ctt cct ctt agc ata tca         2136
Asp Pro Met Val Pro Ser Cys Ser Leu Ser Leu Pro Leu Ser Ile Ser
660                 665                 670 aca aca gag gca gtg tct ttc cac aaa gag aaa agt gtt tat ttg tca         2184
Thr Thr Glu Ala Val Ser Phe His Lys Glu Lys Ser Val Tyr Leu Ser
            675                 680                 685 tca aag ctc aaa caa ctt ctt caa acc caa gat aaa cta act cct cct         2232
Ser Lys Leu Lys Gln Leu Leu Gln Thr Gln Asp Lys Leu Thr Pro Pro
690                 695                 700 gca ggg att tca gca act gaa ata gct aaa tta ggt cct gtt tgt gtg         2280
Ala Gly Ile Ser Ala Thr Glu Ile Ala Lys Leu Gly Pro Val Cys Val
705                 710                 715                 720 tct gct cct gca tca atg ttg cct gtg acc tca agt agg ttt aag agg         2328
Ser Ala Pro Ala Ser Met Leu Pro Val Thr Ser Ser Arg Phe Lys Arg
            725                 730                 735 cgg acc agc tct cct ccc agt tct cca cag cac agt cct gcc ctt cga         2376
Arg Thr Ser Ser Pro Pro Ser Ser Pro Gln His Ser Pro Ala Leu Arg
        740                 745                 750 gac ttt gga aag cca agt gat ggg aaa gca gca tgg acc gat gcc ggg         2424
Asp Phe Gly Lys Pro Ser Asp Gly Lys Ala Ala Trp Thr Asp Ala Gly
            755                 760                 765 ctg act tcc aaa aaa tcc aaa tta gaa agt cac agc gac tca cca gca         2472
Leu Thr Ser Lys Lys Ser Lys Leu Glu Ser His Ser Asp Ser Pro Ala
770                 775                 780 tgg agt ttg tct ggg aga gat gag aga gaa act gtg agc cct cca tgc         2520
Trp Ser Leu Ser Gly Arg Asp Glu Arg Glu Thr Val Ser Pro Pro Cys
785                 790                 795                 800 ttt gat gaa tat aaa atg tct aaa gag tgg aca gct agt tct gct ttt         2568
Phe Asp Glu Tyr Lys Met Ser Lys Glu Trp Thr Ala Ser Ser Ala Phe
            805                 810                 815 agc agt gtg tgc aac cag cag cca ctg gat tta tcc agc ggt gtc aaa         2616
Ser Ser Val Cys Asn Gln Gln Pro Leu Asp Leu Ser Ser Gly Val Lys
        820                 825                 830 cag aag gct gag ggt aca ggc aag act cca gtc cag tgg gaa tct gtc         2664
Gln Lys Ala Glu Gly Thr Gly Lys Thr Pro Val Gln Trp Glu Ser Val
            835                 840                 845 tta gat ctc agt gtg cat aaa aag cat tgt agt gac tct gaa ggc aag         2712
Leu Asp Leu Ser Val His Lys Lys His Cys Ser Asp Ser Glu Gly Lys
850                 855                 860 gaa ttc aaa gaa agt cat tca gtg cag cct acg tgt agt gct gta aag         2760
Glu Phe Lys Glu Ser His Ser Val Gln Pro Thr Cys Ser Ala Val Lys
865                 870                 875                 880 aaa agg aaa cca acc acc tgc atg ctg cag aag gtt ctt ctc aat gaa         2808
Lys Arg Lys Pro Thr Thr Cys Met Leu Gln Lys Val Leu Leu Asn Glu
            885                 890                 895 tat aat ggc atc gat tta cct gta gaa aac cct gca gat ggg acc agg         2856
Tyr Asn Gly Ile Asp Leu Pro Val Glu Asn Pro Ala Asp Gly Thr Arg
        900                 905                 910 agc cca agt cct tgt aaa tcc cta gaa gct cag cca gat cct gac ctc         2904
Ser Pro Ser Pro Cys Lys Ser Leu Glu Ala Gln Pro Asp Pro Asp Leu
            915                 920                 925 ggt ccg ggc tct ggt ttc cct gcc cct act gtt gag tcc aca cct gat         2952
Gly Pro Gly Ser Gly Phe Pro Ala Pro Thr Val Glu Ser Thr Pro Asp
```

-continued

|  |  |  |  |
|---|---|---|---|
| 930 | 935 | 940 | | gtt tgt cct tca tca cct gcc ctg cag aca ccc tcc ctt tca tcc ggt    3000
Val Cys Pro Ser Ser Pro Ala Leu Gln Thr Pro Ser Leu Ser Ser Gly
945                 950                 955                 960 cag ctg cct cct ctc ttg atc ccc aca gat ccc tct tcc cct cca ccc    3048
Gln Leu Pro Pro Leu Leu Ile Pro Thr Asp Pro Ser Ser Pro Pro Pro
                965                 970                 975 tgt ccc ccg gta tta act gtt gcc act ccg ccc cct ccc ctc ctt cct    3096
Cys Pro Pro Val Leu Thr Val Ala Thr Pro Pro Pro Pro Leu Leu Pro
            980                 985                 990 acc gta cct ctt cca gcc ccc tct tcc agt gca tct cca cac cca tgc    3144
Thr Val Pro Leu Pro Ala Pro Ser Ser Ser Ala Ser Pro His Pro Cys
        995                 1000                1005 ccc tct cca ctc tca aat gcc acc gca cag tcc cca ctt cca att ctg    3192
Pro Ser Pro Leu Ser Asn Ala Thr Ala Gln Ser Pro Leu Pro Ile Leu
    1010                1015                1020 tcc cca aca gtg tcc ccc tct ccc tct ccc att cct ccc gtg gag ccc    3240
Ser Pro Thr Val Ser Pro Ser Pro Ser Pro Ile Pro Pro Val Glu Pro
1025                1030                1035                1040 ctg atg tct gcc gcc tca ccc ggg cct cca aca ctt tct tct tcc tcc    3288
Leu Met Ser Ala Ala Ser Pro Gly Pro Pro Thr Leu Ser Ser Ser Ser
                1045                1050                1055 tct tca tct tcc tcc tcc tct tcg ttt tct tct tca tct tcc tcc tct    3336
Ser Ser Ser Ser Ser Ser Ser Phe Ser Ser Ser Ser Ser Ser Ser
            1060                1065                1070 tct cct tct cca cct cct ctc tcc gca ata tca tct gtt gtt tcc tct    3384
Ser Pro Ser Pro Pro Pro Leu Ser Ala Ile Ser Ser Val Val Ser Ser
        1075                1080                1085 ggt gat aat ctg gag gct tct ctc ccc atg ata tct ttc aaa cag gag    3432
Gly Asp Asn Leu Glu Ala Ser Leu Pro Met Ile Ser Phe Lys Gln Glu
    1090                1095                1100 gaa tta gag aat gaa ggt ctg aaa ccc agg gaa gag ccc cag tct gct    3480
Glu Leu Glu Asn Glu Gly Leu Lys Pro Arg Glu Glu Pro Gln Ser Ala
1105                1110                1115                1120 gct gaa cag gat gtt gtt gtt cag gaa aca ttc aac aaa aac ttt gtt    3528
Ala Glu Gln Asp Val Val Val Gln Glu Thr Phe Asn Lys Asn Phe Val
                1125                1130                1135 tgc aac gtc tgt gaa tca cct ttt ctt tcc att aaa gat cta acc aaa    3576
Cys Asn Val Cys Glu Ser Pro Phe Leu Ser Ile Lys Asp Leu Thr Lys
            1140                1145                1150 cat tta tct att cat gct gaa gaa tgg ccc ttc aaa tgt gaa ttt tgt    3624
His Leu Ser Ile His Ala Glu Glu Trp Pro Phe Lys Cys Glu Phe Cys
        1155                1160                1165 gtg cag ctt ttt aag gat aaa acg gac ttg tca gaa cat cgc ttt ttg    3672
Val Gln Leu Phe Lys Asp Lys Thr Asp Leu Ser Glu His Arg Phe Leu
    1170                1175                1180 ctt cat gga gtt ggg aat atc ttt gtg tgt tct gtt tgt aaa aaa gaa    3720
Leu His Gly Val Gly Asn Ile Phe Val Cys Ser Val Cys Lys Lys Glu
1185                1190                1195                1200 ttt gct ttt ttg tgc aat ttg cag cag cac cag cga gat ctc cac cca    3768
Phe Ala Phe Leu Cys Asn Leu Gln Gln His Gln Arg Asp Leu His Pro
                1205                1210                1215 gat aag gtg tgc aca cat cac gag ttt gaa agc ggg act ctg agg ccc    3816
Asp Lys Val Cys Thr His His Glu Phe Glu Ser Gly Thr Leu Arg Pro
            1220                1225                1230 cag aac ttt aca gat ccc agc aag gcc cat gta gag cat atg cag agc    3864
Gln Asn Phe Thr Asp Pro Ser Lys Ala His Val Glu His Met Gln Ser
        1235                1240                1245 ttg cca gaa gat cct tta gaa act tct aaa gaa gaa gag gag tta aat    3912

-continued

```
Leu Pro Glu Asp Pro Leu Glu Thr Ser Lys Glu Glu Glu Leu Asn
    1250                1255                1260 gat tcc tct gaa gag ctt tac acg act ata aaa ata atg gct tct gga       3960
Asp Ser Ser Glu Glu Leu Tyr Thr Thr Ile Lys Ile Met Ala Ser Gly
1265                1270                1275                1280 ata aag aca aaa gat cca gat gtt cga ttg ggc ctc aat cag cat tac       4008
Ile Lys Thr Lys Asp Pro Asp Val Arg Leu Gly Leu Asn Gln His Tyr
                1285                1290                1295 cca agc ttt aaa cca cct cca ttt cag tac cat cac cgt aac ccc atg       4056
Pro Ser Phe Lys Pro Pro Pro Phe Gln Tyr His His Arg Asn Pro Met
            1300                1305                1310 ggg att ggt gtg aca gcc aca aat ttc act aca cac aat att cca cag       4104
Gly Ile Gly Val Thr Ala Thr Asn Phe Thr Thr His Asn Ile Pro Gln
        1315                1320                1325 act ttc act acc gcc att cgc tgc aca aag tgt gga aaa ggt gtc gac       4152
Thr Phe Thr Thr Ala Ile Arg Cys Thr Lys Cys Gly Lys Gly Val Asp
    1330                1335                1340 aat atg ccg gag ttg cac aaa cat atc ctg gct tgt gct tct gca agt       4200
Asn Met Pro Glu Leu His Lys His Ile Leu Ala Cys Ala Ser Ala Ser
1345                1350                1355                1360 gac aag aag agg tac acg cct aag aaa aac cca gta cca tta aaa caa       4248
Asp Lys Lys Arg Tyr Thr Pro Lys Lys Asn Pro Val Pro Leu Lys Gln
                1365                1370                1375 act gtg caa ccc aaa aat ggc gtg gtg gtt tta gat aac tct ggg aaa       4296
Thr Val Gln Pro Lys Asn Gly Val Val Val Leu Asp Asn Ser Gly Lys
            1380                1385                1390 aat gcc ttc cga cga atg gga cag ccc aaa agg ctt aac ttt agt gtt       4344
Asn Ala Phe Arg Arg Met Gly Gln Pro Lys Arg Leu Asn Phe Ser Val
        1395                1400                1405 gag ctc agc aaa atg tcg tcg aat aag ctc aaa tta aat gca ttg aag       4392
Glu Leu Ser Lys Met Ser Ser Asn Lys Leu Lys Leu Asn Ala Leu Lys
    1410                1415                1420 aaa aaa aat cag cta gta cag aaa gca att ctt cag aaa aac aaa tct       4440
Lys Lys Asn Gln Leu Val Gln Lys Ala Ile Leu Gln Lys Asn Lys Ser
1425                1430                1435                1440 gca aag cag aag gcc gac ttg aaa aat gct tgt gag tca tcc tct cac       4488
Ala Lys Gln Lys Ala Asp Leu Lys Asn Ala Cys Glu Ser Ser Ser His
                1445                1450                1455 atc tgc cct tac tgt aat cga gag ttc act tac att gga agc ctg aat       4536
Ile Cys Pro Tyr Cys Asn Arg Glu Phe Thr Tyr Ile Gly Ser Leu Asn
            1460                1465                1470 aaa cac gcc gcc ttc agc tgt ccc aaa aaa ccc ctt tct cct ccc aaa       4584
Lys His Ala Ala Phe Ser Cys Pro Lys Lys Pro Leu Ser Pro Pro Lys
        1475                1480                1485 aaa aaa gtt tct cat tca tct aag aaa ggt gga cac tca tca cct gca       4632
Lys Lys Val Ser His Ser Ser Lys Lys Gly Gly His Ser Ser Pro Ala
    1490                1495                1500 agt agt gac aaa aac agt aac agc aac cac cgc aga cgg aca gcg gat       4680
Ser Ser Asp Lys Asn Ser Asn Ser Asn His Arg Arg Arg Thr Ala Asp
1505                1510                1515                1520 gcg gag att aaa atg caa agc atg cag act ccg ttg ggc aag acc aga       4728
Ala Glu Ile Lys Met Gln Ser Met Gln Thr Pro Leu Gly Lys Thr Arg
                1525                1530                1535 gcc cgc agc tca ggc ccc acc caa gtc cca ctt ccc tcc tca tcc ttc       4776
Ala Arg Ser Ser Gly Pro Thr Gln Val Pro Leu Pro Ser Ser Ser Phe
            1540                1545                1550 agg tcc aag cag aac gtc aag ttt gca gct tcg gtg aaa tcc aaa aaa       4824
Arg Ser Lys Gln Asn Val Lys Phe Ala Ala Ser Val Lys Ser Lys Lys
        1555                1560                1565
```

| | | |
|---|---|---|
| cca agc tcc tcc tct tta agg aac tcc agc ccg ata aga atg gcc aaa<br>Pro Ser Ser Ser Ser Leu Arg Asn Ser Ser Pro Ile Arg Met Ala Lys<br>1570                      1575                    1580 | | 4872 |
| ata act cat gtt gag ggg aaa aaa cct aaa gct gtg gcc aag aat cat<br>Ile Thr His Val Glu Gly Lys Lys Pro Lys Ala Val Ala Lys Asn His<br>1585                    1590                    1595                    1600 | | 4920 |
| tct gct cag ctt tcc agc aaa aca tcg cgg agc ctg cac gtg agg gta<br>Ser Ala Gln Leu Ser Ser Lys Thr Ser Arg Ser Leu His Val Arg Val<br>                  1605                    1610                    1615 | | 4968 |
| cag aaa agc aaa gct gtt tta caa agc aaa tcc acc ttg gcg agt aag<br>Gln Lys Ser Lys Ala Val Leu Gln Ser Lys Ser Thr Leu Ala Ser Lys<br>1620                      1625                    1630 | | 5016 |
| aaa aga aca gac cgg ttc aat ata aaa tct aga gag cgg agt ggg ggg<br>Lys Arg Thr Asp Arg Phe Asn Ile Lys Ser Arg Glu Arg Ser Gly Gly<br>1635                    1640                    1645 | | 5064 |
| cca gtc acc cgg agc ctt cag ctg gca gct gct gct gac ttg agt gag<br>Pro Val Thr Arg Ser Leu Gln Leu Ala Ala Ala Ala Asp Leu Ser Glu<br>1650                      1655                    1660 | | 5112 |
| aac aag aga gag gac ggc agc gcc aag cag gag ctg aag gac ttc agc<br>Asn Lys Arg Glu Asp Gly Ser Ala Lys Gln Glu Leu Lys Asp Phe Ser<br>1665                    1670                    1675                    1680 | | 5160 |
| tac agc ctc cgc ttg gcg tcc cga tgc tct cca cca gcc gcc tct tac<br>Tyr Ser Leu Arg Leu Ala Ser Arg Cys Ser Pro Pro Ala Ala Ser Tyr<br>                  1685                    1690                    1695 | | 5208 |
| atc acc agg cag tat agg aag gtc aaa gct ccg gct gca gcc cag ttc<br>Ile Thr Arg Gln Tyr Arg Lys Val Lys Ala Pro Ala Ala Ala Gln Phe<br>1700                      1705                    1710 | | 5256 |
| cag gga cca ttc ttc aaa gag tagacactct ggctgctccc tgacagcacc<br>Gln Gly Pro Phe Phe Lys Glu<br>        1715 | | 5307 |
| tgaagtgacc tggaatcagt gaagccaaag ggactggcag tctgcctgca gggagtaccg | | 5367 |
| acctatccca gttgtgtgag gctgcgagag aaagggagtg catgtgcgcg cgtgcatgtg | | 5427 |
| tgcgtgcgtg tgtgttcacg tgttctcgtg cgggccgtga gtggtcttca aacgagggtc | | 5487 |
| ccgaaccccg gggcggcagg aaggggggccg actccacgct gtcctttggg atgatacttg | | 5547 |
| gatgtcagct cttgggaccg tgtctgcagc ccagccttcc tgttggggtg gggcctctcc | | 5607 |
| tactatgcaa tttttcaaga gctccttgac cctgctttt gcttcttgag ttgtcttttg | | 5667 |
| ccattatggg gactttggtt tgacccaggg gtcagcccct taggaaggcc ttcaggagga | | 5727 |
| ggccgagttc cccttcagta ccaccccctct ctccccacct gcccgctccc ggcaacatct | | 5787 |
| ctgggaatca acagcatatt gacacgttgg agccgagcct gaacatgccc tgaccccagc | | 5847 |
| acatggaaaa ccccttcct t | | 5868 |

<210> SEQ ID NO 4
<211> LENGTH: 1719
<212> TYPE: PRT
<213> ORGANISM: Homo sapien

<400> SEQUENCE: 4

Met Asn Gln Asn Thr Thr Glu Pro Val Ala Ala Thr Glu Thr Leu Ala
1               5                   10                 15

Glu Val Pro Glu His Val Leu Arg Gly Leu Pro Glu Glu Val Arg Leu
                20                   25                   30

Phe Pro Ser Ala Val Asp Lys Thr Arg Ile Gly Val Trp Ala Thr Lys
            35                   40                   45

Pro Ile Leu Lys Gly Lys Lys Phe Gly Pro Phe Val Gly Asp Lys Lys
    50                   55                   60

-continued

```
Lys Arg Ser Gln Val Lys Asn Asn Val Tyr Met Trp Glu Val Tyr Tyr
 65                  70                  75                  80

Pro Asn Leu Gly Trp Met Cys Ile Asp Ala Thr Asp Pro Lys Gly
                 85                  90                  95

Asn Trp Leu Arg Tyr Val Asn Trp Ala Cys Ser Gly Glu Glu Gln Asn
                100                 105                 110

Leu Phe Pro Leu Glu Ile Asn Arg Ala Ile Tyr Lys Thr Leu Lys
            115                 120                 125

Pro Ile Ala Pro Gly Glu Leu Leu Val Trp Tyr Asn Gly Glu Asp
130                 135                 140

Asn Pro Glu Ile Ala Ala Ile Glu Glu Arg Ala Ser Ala Arg
145                 150                 155                 160

Ser Lys Arg Ser Ser Pro Lys Ser Arg Lys Gly Lys Lys Ser Gln
                165                 170                 175

Glu Asn Lys Asn Lys Gly Asn Lys Ile Gln Asp Ile Gln Leu Lys Thr
                180                 185                 190

Ser Glu Pro Asp Phe Thr Ser Ala Asn Met Arg Asp Ser Ala Glu Gly
            195                 200                 205

Pro Lys Glu Asp Glu Glu Lys Pro Ser Ala Ser Ala Leu Glu Gln Pro
            210                 215                 220

Ala Thr Leu Gln Glu Val Ala Ser Gln Glu Val Pro Pro Glu Leu Ala
225                 230                 235                 240

Thr Pro Ala Pro Ala Trp Glu Pro Gln Pro Glu Pro Asp Glu Arg Leu
                245                 250                 255

Glu Ala Ala Ala Cys Glu Val Asn Asp Leu Gly Glu Glu Glu Glu
                260                 265                 270

Glu Glu Glu Glu Asp Glu Glu Glu Glu Asp Asp Asp Asp Glu
            275                 280                 285

Leu Glu Asp Glu Gly Glu Glu Ala Ser Met Pro Asn Glu Asn Ser
            290                 295                 300

Val Lys Glu Pro Glu Ile Arg Cys Asp Glu Lys Pro Glu Asp Leu Leu
305                 310                 315                 320

Glu Glu Pro Lys Thr Thr Ser Glu Glu Thr Leu Glu Asp Cys Ser Glu
                325                 330                 335

Val Thr Pro Ala Met Gln Ile Pro Arg Thr Lys Glu Glu Ala Asn Gly
                340                 345                 350

Asp Val Phe Glu Thr Phe Met Phe Pro Cys Gln His Cys Glu Arg Lys
                355                 360                 365

Phe Thr Thr Lys Gln Gly Leu Glu Arg His Met His Ile His Ile Ser
            370                 375                 380

Thr Val Asn His Ala Phe Lys Cys Lys Tyr Cys Gly Lys Ala Phe Gly
385                 390                 395                 400

Thr Gln Ile Asn Arg Arg Arg His Glu Arg Arg His Glu Ala Gly Leu
                405                 410                 415

Lys Arg Lys Pro Ser Gln Thr Leu Gln Pro Ser Glu Asp Leu Ala Asp
            420                 425                 430

Gly Lys Ala Ser Gly Glu Asn Val Ala Ser Lys Asp Ser Ser Pro
            435                 440                 445

Pro Ser Leu Gly Pro Asp Cys Leu Ile Met Asn Ser Glu Lys Ala Ser
            450                 455                 460

Gln Asp Thr Ile Asn Ser Ser Val Val Glu Glu Asn Gly Glu Val Lys
465                 470                 475                 480
```

-continued

```
Glu Leu His Pro Cys Lys Tyr Cys Lys Val Phe Gly Thr His Thr
            485                 490                 495

Asn Met Arg Arg His Gln Arg Arg Val His Glu Arg His Leu Ile Pro
            500                 505                 510

Lys Gly Val Arg Arg Lys Gly Gly Leu Glu Glu Pro Gln Pro Pro Ala
            515                 520                 525

Glu Gln Ala Gln Ala Thr Gln Asn Val Tyr Val Pro Ser Thr Glu Pro
            530                 535                 540

Glu Glu Glu Gly Glu Ala Asp Asp Val Tyr Ile Met Asp Ile Ser Ser
545                 550                 555                 560

Asn Ile Ser Glu Asn Leu Asn Tyr Tyr Ile Asp Gly Lys Ile Gln Thr
            565                 570                 575

Asn Asn Asn Thr Ser Asn Cys Asp Val Ile Glu Met Glu Ser Ala Ser
            580                 585                 590

Ala Asp Leu Tyr Gly Ile Asn Cys Leu Leu Thr Pro Val Thr Val Glu
            595                 600                 605

Ile Thr Gln Asn Ile Lys Thr Thr Gln Val Pro Val Thr Glu Asp Leu
            610                 615                 620

Pro Lys Glu Pro Leu Gly Ser Thr Asn Ser Glu Ala Lys Lys Arg Arg
625                 630                 635                 640

Thr Ala Ser Pro Pro Ala Leu Pro Lys Ile Lys Ala Glu Thr Asp Ser
            645                 650                 655

Asp Pro Met Val Pro Ser Cys Ser Leu Ser Leu Pro Leu Ser Ile Ser
            660                 665                 670

Thr Thr Glu Ala Val Ser Phe His Lys Glu Lys Ser Val Tyr Leu Ser
            675                 680                 685

Ser Lys Leu Lys Gln Leu Leu Gln Thr Gln Asp Lys Leu Thr Pro Pro
            690                 695                 700

Ala Gly Ile Ser Ala Thr Glu Ile Ala Lys Leu Gly Pro Val Cys Val
705                 710                 715                 720

Ser Ala Pro Ala Ser Met Leu Pro Val Thr Ser Ser Arg Phe Lys Arg
            725                 730                 735

Arg Thr Ser Ser Pro Pro Ser Ser Pro Gln His Ser Pro Ala Leu Arg
            740                 745                 750

Asp Phe Gly Lys Pro Ser Asp Gly Lys Ala Ala Trp Thr Asp Ala Gly
            755                 760                 765

Leu Thr Ser Lys Lys Ser Lys Leu Glu Ser His Ser Asp Ser Pro Ala
    770                 775                 780

Trp Ser Leu Ser Gly Arg Asp Glu Arg Glu Thr Val Ser Pro Pro Cys
785                 790                 795                 800

Phe Asp Glu Tyr Lys Met Ser Lys Glu Trp Thr Ala Ser Ser Ala Phe
            805                 810                 815

Ser Ser Val Cys Asn Gln Gln Pro Leu Asp Leu Ser Ser Gly Val Lys
            820                 825                 830

Gln Lys Ala Glu Gly Thr Gly Lys Thr Pro Val Gln Trp Glu Ser Val
            835                 840                 845

Leu Asp Leu Ser Val His Lys Lys His Cys Ser Asp Ser Glu Gly Lys
    850                 855                 860

Glu Phe Lys Glu Ser His Ser Val Gln Pro Thr Cys Ser Ala Val Lys
865                 870                 875                 880

Lys Arg Lys Pro Thr Thr Cys Met Leu Gln Lys Val Leu Leu Asn Glu
            885                 890                 895

Tyr Asn Gly Ile Asp Leu Pro Val Glu Asn Pro Ala Asp Gly Thr Arg
```

-continued

```
                900                 905                 910
Ser Pro Ser Pro Cys Lys Ser Leu Glu Ala Gln Pro Asp Pro Asp Leu
        915                 920                 925

Gly Pro Gly Ser Gly Phe Pro Ala Pro Thr Val Glu Ser Thr Pro Asp
        930                 935                 940

Val Cys Pro Ser Ser Pro Ala Leu Gln Thr Pro Ser Leu Ser Ser Gly
945                 950                 955                 960

Gln Leu Pro Pro Leu Leu Ile Pro Thr Asp Pro Ser Ser Pro Pro Pro
        965                 970                 975

Cys Pro Pro Val Leu Thr Val Ala Thr Pro Pro Pro Leu Leu Pro
        980                 985                 990

Thr Val Pro Leu Pro Ala Pro Ser Ser Ser Ala Ser Pro His Pro Cys
        995                 1000                1005

Pro Ser Pro Leu Ser Asn Ala Thr Ala Gln Ser Pro Leu Pro Ile Leu
        1010                1015                1020

Ser Pro Thr Val Ser Pro Ser Pro Ser Pro Ile Pro Val Glu Pro
1025                1030                1035                1040

Leu Met Ser Ala Ala Ser Pro Gly Pro Pro Thr Leu Ser Ser Ser Ser
                1045                1050                1055

Ser Ser Ser Ser Ser Ser Ser Ser Phe Ser Ser Ser Ser Ser Ser Ser
                1060                1065                1070

Ser Pro Ser Pro Pro Pro Leu Ser Ala Ile Ser Ser Val Val Ser Ser
        1075                1080                1085

Gly Asp Asn Leu Glu Ala Ser Leu Pro Met Ile Ser Phe Lys Gln Glu
        1090                1095                1100

Glu Leu Glu Asn Glu Gly Leu Lys Pro Arg Glu Glu Pro Gln Ser Ala
1105                1110                1115                1120

Ala Glu Gln Asp Val Val Gln Glu Thr Phe Asn Lys Asn Phe Val
        1125                1130                1135

Cys Asn Val Cys Glu Ser Pro Phe Leu Ser Ile Lys Asp Leu Thr Lys
                1140                1145                1150

His Leu Ser Ile His Ala Glu Glu Trp Pro Phe Lys Cys Glu Phe Cys
        1155                1160                1165

Val Gln Leu Phe Lys Asp Lys Thr Asp Leu Ser Glu His Arg Phe Leu
        1170                1175                1180

Leu His Gly Val Gly Asn Ile Phe Val Cys Ser Val Cys Lys Lys Glu
1185                1190                1195                1200

Phe Ala Phe Leu Cys Asn Leu Gln Gln His Gln Arg Asp Leu His Pro
                1205                1210                1215

Asp Lys Val Cys Thr His His Glu Phe Glu Ser Gly Thr Leu Arg Pro
                1220                1225                1230

Gln Asn Phe Thr Asp Pro Ser Lys Ala His Val Glu His Met Gln Ser
        1235                1240                1245

Leu Pro Glu Asp Pro Leu Glu Thr Ser Lys Glu Glu Glu Leu Asn
        1250                1255                1260

Asp Ser Ser Glu Glu Leu Tyr Thr Thr Ile Lys Ile Met Ala Ser Gly
1265                1270                1275                1280

Ile Lys Thr Lys Asp Pro Asp Val Arg Leu Gly Leu Asn Gln His Tyr
                1285                1290                1295

Pro Ser Phe Lys Pro Pro Pro Phe Gln Tyr His His Arg Asn Pro Met
        1300                1305                1310

Gly Ile Gly Val Thr Ala Thr Asn Phe Thr Thr His Asn Ile Pro Gln
        1315                1320                1325
```

```
Thr Phe Thr Thr Ala Ile Arg Cys Thr Lys Cys Gly Lys Gly Val Asp
    1330                1335                1340
Asn Met Pro Glu Leu His Lys His Ile Leu Ala Cys Ala Ser Ala Ser
1345                1350                1355                1360
Asp Lys Lys Arg Tyr Thr Pro Lys Lys Asn Pro Val Pro Leu Lys Gln
                1365                1370                1375
Thr Val Gln Pro Lys Asn Gly Val Val Val Leu Asp Asn Ser Gly Lys
            1380                1385                1390
Asn Ala Phe Arg Arg Met Gly Gln Pro Lys Arg Leu Asn Phe Ser Val
        1395                1400                1405
Glu Leu Ser Lys Met Ser Ser Asn Lys Leu Lys Leu Asn Ala Leu Lys
    1410                1415                1420
Lys Lys Asn Gln Leu Val Gln Lys Ala Ile Leu Gln Lys Asn Lys Ser
1425                1430                1435                1440
Ala Lys Gln Lys Ala Asp Leu Lys Asn Ala Cys Glu Ser Ser His
                1445                1450                1455
Ile Cys Pro Tyr Cys Asn Arg Glu Phe Thr Tyr Ile Gly Ser Leu Asn
            1460                1465                1470
Lys His Ala Ala Phe Ser Cys Pro Lys Lys Pro Leu Ser Pro Pro Lys
        1475                1480                1485
Lys Lys Val Ser His Ser Ser Lys Lys Gly His Ser Ser Pro Ala
    1490                1495                1500
Ser Ser Asp Lys Asn Ser Asn Ser Asn His Arg Arg Arg Thr Ala Asp
1505                1510                1515                1520
Ala Glu Ile Lys Met Gln Ser Met Gln Thr Pro Leu Gly Lys Thr Arg
                1525                1530                1535
Ala Arg Ser Ser Gly Pro Thr Gln Val Pro Leu Pro Ser Ser Ser Phe
            1540                1545                1550
Arg Ser Lys Gln Asn Val Lys Phe Ala Ala Ser Val Lys Ser Lys Lys
        1555                1560                1565
Pro Ser Ser Ser Leu Arg Asn Ser Ser Pro Ile Arg Met Ala Lys
    1570                1575                1580
Ile Thr His Val Glu Gly Lys Lys Pro Lys Ala Val Ala Lys Asn His
1585                1590                1595                1600
Ser Ala Gln Leu Ser Ser Lys Thr Ser Arg Ser Leu His Val Arg Val
                1605                1610                1615
Gln Lys Ser Lys Ala Val Leu Gln Ser Lys Ser Thr Leu Ala Ser Lys
            1620                1625                1630
Lys Arg Thr Asp Arg Phe Asn Ile Lys Ser Arg Glu Arg Ser Gly Gly
        1635                1640                1645
Pro Val Thr Arg Ser Leu Gln Leu Ala Ala Ala Asp Leu Ser Glu
    1650                1655                1660
Asn Lys Arg Glu Asp Gly Ser Ala Lys Gln Glu Leu Lys Asp Phe Ser
1665                1670                1675                1680
Tyr Ser Leu Arg Leu Ala Ser Arg Cys Ser Pro Pro Ala Ala Ser Tyr
                1685                1690                1695
Ile Thr Arg Gln Tyr Arg Lys Val Lys Ala Pro Ala Ala Ala Gln Phe
            1700                1705                1710
Gln Gly Pro Phe Phe Lys Glu
        1715

<210> SEQ ID NO 5
<211> LENGTH: 116
```

```
<212> TYPE: PRT
<213> ORGANISM: Homo sapien

<400> SEQUENCE: 5

Val Asp Lys Thr Arg Ile Gly Val Trp Ala Thr Lys Pro Ile Leu Lys
 1               5                  10                  15

Gly Lys Lys Phe Gly Pro Phe Val Gly Asp Lys Lys Arg Ser Gln
                20                  25                  30

Val Lys Asn Asn Val Tyr Met Trp Glu Val Tyr Tyr Pro Asn Leu Gly
             35                  40                  45

Trp Met Cys Ile Asp Ala Thr Asp Pro Glu Lys Gly Asn Trp Leu Arg
     50                  55                  60

Tyr Val Asn Trp Ala Cys Ser Gly Glu Glu Gln Asn Leu Phe Pro Leu
65                   70                  75                  80

Glu Ile Asn Arg Ala Ile Tyr Tyr Lys Thr Leu Lys Pro Ile Ala Pro
                 85                  90                  95

Gly Glu Glu Leu Leu Val Trp Tyr Asn Gly Asp Asn Pro Glu Ile
            100                 105                 110

Ala Ala Ala Ile
        115

<210> SEQ ID NO 6
<211> LENGTH: 21
<212> TYPE: PRT
<213> ORGANISM: Homo sapien

<400> SEQUENCE: 6

Glu Trp Gly Pro Val Thr Arg Ser Leu Gln Arg Ser Thr Lys Gln Glu
 1               5                  10                  15

Leu Lys Asp Leu Gln
            20

<210> SEQ ID NO 7
<211> LENGTH: 22
<212> TYPE: PRT
<213> ORGANISM: Homo sapien

<400> SEQUENCE: 7

Gly Ala Glu Glu Thr Ala Ala Ala Ala Ala Leu Gly Ala Leu Arg
 1               5                  10                  15

Leu Gly Arg Arg Ala Arg
            20

<210> SEQ ID NO 8
<211> LENGTH: 391
<212> TYPE: DNA
<213> ORGANISM: Mus musculus
<220> FEATURE:
<221> NAME/KEY: CDS
<222> LOCATION: (1)...(390)

<400> SEQUENCE: 8 gtg tac tac cca aat ttg ggg tgg atg tgc att gat gcc act gat ccg      48
Val Tyr Tyr Pro Asn Leu Gly Trp Met Cys Ile Asp Ala Thr Asp Pro
 1               5                  10                  15 gag aag ggc aac tgg ctc cgc tat gtg aac tgg gct tgc tca gga gaa      96
Glu Lys Gly Asn Trp Leu Arg Tyr Val Asn Trp Ala Cys Ser Gly Glu
                20                  25                  30 gaa cag aat tta ttt cca ctg gaa atc aac aga gcc att tac tat aaa     144
Glu Gln Asn Leu Phe Pro Leu Glu Ile Asn Arg Ala Ile Tyr Tyr Lys
             35                  40                  45
```

```
acc tta aag cca atc gcg cct ggc gag gag ctc ctg gtc tgg tac aat      192
Thr Leu Lys Pro Ile Ala Pro Gly Glu Glu Leu Leu Val Trp Tyr Asn
     50                  55                  60 ggg gaa gac aac ccc gag ata gca gct gcg att gag gaa gag cga gcc      240
Gly Glu Asp Asn Pro Glu Ile Ala Ala Ala Ile Glu Glu Glu Arg Ala
 65                  70                  75                  80 agc gcc cgg agc aag cgg agc tcc ccg aag agc cgg aga ggg aag aag      288
Ser Ala Arg Ser Lys Arg Ser Ser Pro Lys Ser Arg Arg Gly Lys Lys
                 85                  90                  95 aaa tca cag gag aat aaa aac aaa ggc atc aga acc cag gct gca gcg      336
Lys Ser Gln Glu Asn Lys Asn Lys Gly Ile Arg Thr Gln Ala Ala Ala
            100                 105                 110 cgg aag gcg agc gag ctg gac tcc acc tct gca aac atg agg ggc tct      384
Arg Lys Ala Ser Glu Leu Asp Ser Thr Ser Ala Asn Met Arg Gly Ser
        115                 120                 125 gca gaa g                                                            391
Ala Glu
    130
```

```
<210> SEQ ID NO 9
<211> LENGTH: 130
<212> TYPE: PRT
<213> ORGANISM: Mus musculus

<400> SEQUENCE: 9

Val Tyr Tyr Pro Asn Leu Gly Trp Met Cys Ile Asp Ala Thr Asp Pro
 1               5                  10                  15

Glu Lys Gly Asn Trp Leu Arg Tyr Val Asn Trp Ala Cys Ser Gly Glu
            20                  25                  30

Glu Gln Asn Leu Phe Pro Leu Glu Ile Asn Arg Ala Ile Tyr Tyr Lys
        35                  40                  45

Thr Leu Lys Pro Ile Ala Pro Gly Glu Glu Leu Leu Val Trp Tyr Asn
    50                  55                  60

Gly Glu Asp Asn Pro Glu Ile Ala Ala Ala Ile Glu Glu Glu Arg Ala
 65                  70                  75                  80

Ser Ala Arg Ser Lys Arg Ser Ser Pro Lys Ser Arg Arg Gly Lys Lys
                 85                  90                  95

Lys Ser Gln Glu Asn Lys Asn Lys Gly Ile Arg Thr Gln Ala Ala Ala
            100                 105                 110

Arg Lys Ala Ser Glu Leu Asp Ser Thr Ser Ala Asn Met Arg Gly Ser
        115                 120                 125

Ala Glu
    130
```

```
<210> SEQ ID NO 10
<211> LENGTH: 18
<212> TYPE: DNA
<213> ORGANISM: Artificial Sequence
<220> FEATURE:
<223> OTHER INFORMATION: synthetic primer

<400> SEQUENCE: 10
tgtaaaacga cggccagt                                                   18
```

```
<210> SEQ ID NO 11
<211> LENGTH: 18
<212> TYPE: DNA
<213> ORGANISM: Artificial Sequence
<220> FEATURE:
<223> OTHER INFORMATION: synthetic primer
```

```
<400> SEQUENCE: 11
caggaaacag ctatgacc                                                       18

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
gagctcagca aaatgtcgtc                                                     20

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
caagtcggcc ttctgctttg                                                     20

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
tctcacatct gcccttactg                                                     20

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
gtgatgagtg tccacctttc                                                     20
```